US005767376A

United States Patent [19]
Stiles et al.

[11] Patent Number: 5,767,376
[45] Date of Patent: Jun. 16, 1998

[54] NUCLEIC ACIDS ENCODING A PAPAYA ACC SYNTHASE GENE

[75] Inventors: John I. Stiles, Kaneohe; Kabi Raj Neupane, Honolulu, both of Hi.

[73] Assignee: University of Hawaii at Manoa, Honolulu, Hi.

[21] Appl. No.: 485,107

[22] Filed: Jun. 7, 1995

[51] Int. Cl.$^6$ .............................. A01H 5/00; C12N 15/63; E12N 5/04; C07H 21/04
[52] U.S. Cl. ...................... 800/205; 435/320.1; 435/419; 536/23.6
[58] Field of Search .................. 536/23.6; 435/172.3, 435/320.1, 419; 800/205

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,826,765 | 5/1989 | Greene et al. | 435/69.1 |
| 5,107,065 | 4/1992 | Shewmaker et al. | 800/205 |
| 5,187,267 | 2/1993 | Comai et al. | 536/23.1 |
| 5,283,184 | 2/1994 | Jorgensen et al. | 435/172.3 |

FOREIGN PATENT DOCUMENTS

| | | |
|---|---|---|
| WO 84/02913 | 8/1984 | WIPO. |
| WO 88/09334 | 12/1988 | WIPO. |
| WO 84/02919 | 8/1994 | WIPO. |
| WO 84/02920 | 8/1994 | WIPO. |

OTHER PUBLICATIONS

Napoli et al. Introduction of a chimeric chalcone synthase gene into petunia results in reversible co-suppression of homologous genes in trans. The Plant Cell. 2:279–289, Apr., 1990.

Smith et al. Antisense RNA inhibition of polygalacturonase gene expression in transgenic tomatoes. Nature. 334:724–726, 25 Aug. 1988.

Raven, P., et al., *Biology of Plants*, 5th ed., Worth Publishers, p. 554, (1992).

Theologis, "One Rotten Apple Spoils the Whole Bushel: The Role of Ethylene in Fruit Ripening," *Cell* 70:181–184 (1992).

Yang and Hoffman, "Ethylene Biosynthesis And Its Regulation In Higher Plants", *Ann. Rev. Physiol.* 35:155 (1984).

Wardlaw, "Iodine And The Control Of Fungal Wastage", *Tropical Agriculture*, 24:288 (1936).

Jones and Kubota, "Some Chemical and Respirational Changes In The Papaya Fruit During Ripening, And The Effects of Cold Storage On These Changes", *Plant Physiol.*, 15:711 (1940).

Akamine and Goo, "Concentrations of Carbon Dioxide and Ethylene In The Cavity of Attached Papaya Fruit", *Hort. Science*, 14:138 (1979).

Paull and Chen, "Post Harvest Variation in Cell Wall–Degrading Enzymes of Papaya (*Carica papaya* L.) During Fruit Ripening", Plant Physiol., 72:382 (1983).

Burg, Ann. Rev. "The Physiology Of Ethylene Formation", *Plant Physiol.*, 13:265–302 (1962).

Burg and Burg, "Fruit Storage at Subatmospheric Pressures", *Science* 153:314–315 (1966).

Gray et al., "Molecular Biology of Fruit Ripening And Its Manipulation With Antisense Genes," *Plant Mol. Biol.*, 19:69–87 (1992).

Theologis et al., "Modifying Fruit Ripening by Suppressing Gene Expression," in *Cellular and Molecular Aspects of Plant Hormone Ethylene*, J.C. Pech et al., (eds.), Kluwer Academic Publishers, pp. 19–23 (1993).

Imaseki, "The Biochemistry of Ethylene Biosynthesis," in *The Plant Hormone Ethylene, Matto and Suttle* (eds.) CRC Press, Inc., Boca Raton, pp. 1–20 (1991).

Kende, "Ethylene Biosynthesis", *Ann. Rev. Plant Physiol.*, 44:283 (1993).

Oeller et al., "Reversible Inhibition of Tomato Fruit Senescence by Antisense RNA," *Science* 254:437 (1991).

Theologis et al., "Use of a Tomato Mutant Constructed With Reverse Genetics to Study Fruit Ripening, a Complex Developmental Process," *Develop, Genet.* 14:282–295 (1993).

Sambrook et al., *Molecular Cloning: A Laboratory Manual*, 2nd ed., Cold Spring Harbor Laboratory Press, New York (1989) pp. 6.30–6.31 7.39–7.52 9.31–9.58 16.7–16.15.

Kacian et al., "A Replicating RNA Molecule Suitable for a Detailed Analysis of Extracellular Evolutionand Replication", *Proc. Natl. Acad. Sci USA*, 69:3038 (1972).

Chamberlain et al., "New RNA Polymerase from *Escherichia coli* Infected With Bacteriophage T7," *Nature* 228:227 (1970).

Wu and Wallace, "The Ligation Amplification Reaction (LAR)—Amplification of Specific DNA Sequences Using Sequential Rounds of Template–Dependent Ligation," *Genomics* 4:560 (1989).

*PCR Technology*, H.A. Erlich (ed.) Stockton Press pp. 7–16 (1989).

Maniatis et al., "Regulation of Inducible and Tissue–Specific Gene Expression," *Science* 236:1237 (1987).

Fitch et al., "Stable Transformation of Papaya Via Microprojectile Bombardment", *Plant Cell Rep.* 9:189 (1990).

Fitch et al., "High Frequency Somatic Embryogenesis and Plant Regeneration From Papaya Hypocotyl Callus", *Plant Cell Tiss. Org. Cult.* 32:205 (1993).

Napoli et al., "Introduction Of A Chimeric Chalcone Synthase Gene Into Petunia Results in Reversible Co–Suppression of Homologous Genes in trans", *Plant Cell.* 2:279 (1990).

(List continued on next page.)

*Primary Examiner*—Douglas W. Robinson
*Assistant Examiner*—Thanda Wai
*Attorney, Agent, or Firm*—Medlen & Carroll, LLP

[57] ABSTRACT

The present invention provides 1-aminocyclopropane-1-carboxylic acid synthase (ACC synthase) cDNA sequences from papaya fruit. These sequences are useful in regulation of ethylene biosynthesis in papaya cells and in regulating fruit ripening, including delaying of ripening. This is accomplished by co-suppression or by antisense technology. The present invention also provides methods for regulation of fruit ripening.

13 Claims, 5 Drawing Sheets

OTHER PUBLICATIONS

Smith et al., "Antisense RNA Inhibition of Polygalacturonase Gene Expression In Transgenic Tomatoes," *Nature* 334:724 (1988).

Knutzon et al., "Modification of Brassica Seed Oil by Antisense Expression Of A Stearoyl–Acyl Carrier Protein Desaturase Gene", *Proc. Natl. Acad. Sci. USA* 89:2624–2628 (1992).

van der Krol et al., "An Anti–Sense Chalcone Synthase Gene in Transgenic Plants Inhibits Flower Pigmentation," *Nature* 333:866–869 (1988).

Visser et al., "Inhibition of The Expression Of The Gene For Granule–Bound Starch Synthase in Potatoe By Antisense Constructs", *Mol. and Gen. Gene.* 225:289–296 (1991).

Tieman et al., "An Antisense Pectin Methylesterase Gene Alters Pectin Chemistry And Soluble Solids in Tomato Fruit", *Plant Cell* 4:667–679 (1992).

van der Krol et al., "Flavonid Genes in Petunia: Addition Of A Limited Number of Gene Copies May Lead To A Suppression Of Gene Expression", *Plant Cell* 2:291 (1990).

Matzke and Matzke, "How and Why Do Plants Inactivate Homologous (Trans)genes?" *Plant Physiol.* 107:679 (1995).

Fromm et al., "Expression Of Genes Transferred Into Monocot And Dicot Plant Cells By Electroportation", *PNAS* 82:5824–5828 (1985).

Horsch et al., "A Simple And General Method For Transferring Genes Into Plants", *Science* 227:1229–1231 (1985).

Herrera–Estrella et al., "Expression of Chimaeric Genes Transferred into Plant Cells Using A Ti–Plasmid–Derived Vector", *Nature* 303:209–313 (1983).

Crossway et al., "Micromanipulation Techniques in Plant Biotechnology," *Biotechniques* 4:320–334 (1986).

Lin, "Microinjection Of Mouse Egg", *Science* 151:333–337 (1966).

Steinbiss and Stabel, "Protoplast Derived Tobacco Cells Can Survive Capillary Microinjection Of The Flourescent Dye Lucifer Yellow", *Protoplasma,* 116:222–227 (1983).

Charest et al., "Microprojectile–DNA Delivery In Conifer Species: Factors Affecting Assesment of Transient Gene Expression Using The β–Glucuronidase Reporter Gene", *Plant Cell Rep.* 12:189 (1993).

Russell et al., "Major Improvements In Biolistic Transformation Of Suspension–Cultured Tobacco Cells", in vitro Cell Develop. Biol. 28P:97 (1992).

Su and Gibor, "A Method for RNA Isolation From Marine Macro–Algae", *Analytical Biochem.* 174:650 (1988).

Lopez–Gomez and Gomez–Lim, "Changes in mRNA and Protein Synthesis During Ripening in Mango Fruit", *J. Plant Physiol.* 141:82 (1992).

Neill et al., "Expression Of A Wheat α–Gliadin Gene in *Saccharomyces cerevisiae*", *Gene* 55:303 (1985).

Hamilton et al., "Identification of a Tomato Gene For The Ethylene–Forming Enzyme By Expression In Yeast," *Proc. Natl. Acad. Sci. USA* 88:7434 (1991).

Spanu et al., "Analysis And Cloning Of The Ethylene–Forming Enzyme From Tomato By Functional Expression of Its mRNA in *Xenopus laevis Oocytes*", *EMBO J.* 10:2007 (1991).

Dale and Ow, "Gene Transfer With Subsequent Removal Of The Selection Gene From The Host Genome," *Proc Natl Acad. Sci. USA* 88:10558 (1991).

Jorgensen, "Altered Gene Expression In Plants Due to Trans Interactions Between Homologous Genes," *Trends in Biotechnology,* 8:340–344 (1990).

Grierson et al., "Does Co–Suppression Of Sense Genes In Transgenic Plants Involve Antisense RNA?," *Trends in Biotechnology,* 9:122 (1991).

Comai et al., "A New Technique For Genetic Engineering Of Agrobacterium Ti Plasmid", *Plasmid* 10:21–30 (1983).

FIGURE 1

```
   1 TTGAGCTAGA AAGAAAATGG TGCTAATGTT GAGAAATCAA GAGCTGTTGT
  51 CCAAGATTGC AACCAGCAAC GGACATGGCG AGGACTCTCC CTACTTTGAT
 101 GGGTGGAAAG CATACGACAG TGACCCTTTT CATCCTACAC AGAATCCAGA
 151 AGGAGTTATA CAGATGGGTC TTGCAGAGAA TCAGCTTTGC TTTAATTTAA
 201 TTCACGAGTG GCTGCTGAAA AACCCAGAAG CCTCCATTTG TACAGCACAA
 251 GGAGCAGCTG AATTCAGAGA TATAGCTATC TTTCAAGATT ATCATGGCTT
 301 GGCTGAATTC AGAGAGGCTG TTGCAAAGTT TATGGGGAAA GTGAGAAGAA
 351 ACAGAGCTTC ATTTGACCCT GATCGGATTG TTATGAGTGG AGGAGCAACT
 401 GGAGCTCATG AAATGATTGC TTTCTGTTTG GCTGATCCTG GCGATGCATT
 451 CTTGGTTCCA ACTCCTTATT ATCCAGGGTT TGATAGAGAT TTGAGATGGA
 501 GAACGGGAGT CAAACTCATT CCAGTTGTCT GTGAAAGCTC AAACGATTAC
 551 CAGATCACCA TAGAAGCCCT GGAAGCTGCT TATGAAACCG CACAAGAAGC
 601 TGACATCAAG GTAAAGGGTT TGCTCATACC CAACCCATCA AACCCACTGG
 651 GAACAATTAT TACCAAGGAC ACATTAGAAG CTCTAGTCAC CTTCACCAAC
 701 CACAAGAACA TTCATCTGGT GTGTGATGAG ATATATGCTG CTACCGTCTT
 751 CAGCCAGCCC GAATTCACCA GCATAGCCGA GATAATTGAA GAAGATAAAA
 801 TTTGTTGCAA TCGTGATCTC ATCCACATCA TTTACAGTTT ATCCAAAGAC
 851 ATGGGATTCC CTGGATTTAG AGTTGGCATT GTGTATTCAT ACAATGATGC
 901 AGTGGTGAGT TGTGCTCGTA AGATGTCGAG CTTCGGCCTA GTATCTTCGC
 951 AAACCCAGTA TCTGATTGCA TCCATGTTAG CAGACGATGA ATTTGTAGAC
1001 CAATTTATTG TAGAGAGCAG AAAGAGGCTG GCAATGAGAC ATAGTTTTTT
1051 CACACAAAGA CTTGCTCAAG TAGGCATTAA CTGTTTAAAA AGCAATGCTG
1101 GTCTTTTTGT GTGGATGGAT TTGCGTAGAC TGCTGAAAGA ACAGACATTT
1151 GAAGCAGAAA TGGTGTTATG GAGAGTAATT ATAAACGAAA TAAAACTCAA
1201 TGTATCTCCT GGTTCGTCTT TCCACTGCTC AGAACCTGGC TGGTTCAGGG
1251 TTTGCTTTGC AAACATGGAC GATAAGACAA TGGAAATTGC ACTGTCAAGA
1301 ATCAAAACCT TCATGCTTCA ACATAAGGAA GCAATGGTGC CTAAAAAGAA
1351 ACTTTGCTGG CAAACTAGTC TTAGACTCAG CTTCTCCTCT CGCTATGAGG
1401 ATATCATGGA GACACCGGGT TCGTTCATGT CTCCTCACTC GCCTATACCT
1451 CAATCACCTC TTGTTCGAGC CAGGACATAG ATCCAAATAC TTATGATCAC
1501 AACCAGTTTT CAGATGATGA TGATGATAAT ATGTCGATTC GTTGGGTGAT
1551 GATTCGAGTG ATCGTGCATC AGGGCGATCT AGTTGACAAG TTAGCTAATT
1601 ATATTTTGAT CTTGTTAGAA TCATGTGTAA ATAAGAGAAA GTTGGTGCAT
1651 TCTTTTCCAG TTACAGATCA ATTGATCATA TTCTACTGGT TTATAAGCAC
1701 ACAACTATGT TTATTTATTT ATTTTTTTAA TAATTTTTTT TCACATACAA
1751 CAAGTGTAGG TGAAAAAATA TTTAAGTGTT TGTTTGTGTG CGTTGCTCAA
1801 GCACGTTACA CCTATCATGT CTTCCTTCCT AATTATTTTA TATGTCATGA
1851 TCAAGTTAAT TTTATTTTAA AAAAAAAAA AAAAAAA
```

FIGURE 2

| Primer | Extends toward | Sequence |
| --- | --- | --- |
| ACS 167 | 3' end | 5'-GCCGAATTCATGGGAN(C/T)TNGCNGA(A/G)AA(T/C)CA-3' (SEQ ID NO:5) |
| ACS 289 | 3' end | 5'-TT(T/C)CA(G/A)GA(C/T)TA(T/C)CA(T/C)GG(T/C/A)(T/C)T-3' (SEQ ID NO:6) |
| ACS 309 | 5' end | 5'-GCCAAGCTTCC(A/G)TG(A/G)TA(A/G)TC(T/C)TG(A/G)AA-3' (SEQ ID NO:7) |
| ACS 665 | 5' end | 5'-GG(A/G)TT(A/G/T)(C/G)ANGG(A/G)TTNGT(G/C)A-3' (SEQ ID NO:8) |
| ACS 885 | 5' end | 5'-CC(C/A/T)GG(G/A)A(G/A)A(G/A)NCC(T/C)A(A/T)(G/A)TCTTT-3' (SEQ ID NO:9) |
| ACS 1290 | 5' end | 5'-AT(A/G)TT(A/T/G)GC(G/A)AA(GA)CA(AC)A(C/T/G)(T/C/G)C(G/T)(A/G)ACCA 3' (SEQ ID NO:10) |

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1888 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 17..1480

( x i ) SEQUENCE DESCRIPTION: SEQ ID NO:1:

```
TTGAGCTAGA AAGAAA ATG GTG CTA ATG TTG AGA AAT CAA GAG CTG TTG              49
               Met Val Leu Met Leu Arg Asn Gln Glu Leu Leu
                1               5                  10

TCC AAG ATT GCA ACC AGC AAC GGA CAT GGC GAG GAC TCT CCC TAC TTT            97
Ser Lys Ile Ala Thr Ser Asn Gly His Gly Glu Asp Ser Pro Tyr Phe
            15              20                  25

GAT GGG TGG AAA GCA TAC GAC AGT GAC CCT TTT CAT CCT ACA CAG AAT           145
Asp Gly Trp Lys Ala Tyr Asp Ser Asp Pro Phe His Pro Thr Gln Asn
        30                  35                  40

CCA GAA GGA GTT ATA CAG ATG GGT CTT GCA GAG AAT CAG CTT TGC TTT           193
Pro Glu Gly Val Ile Gln Met Gly Leu Ala Glu Asn Gln Leu Cys Phe
    45                  50                  55

AAT TTA ATT CAC GAG TGG CTG CTG AAA AAC CCA GAA GCC TCC ATT TGT           241
Asn Leu Ile His Glu Trp Leu Leu Lys Asn Pro Glu Ala Ser Ile Cys
60                  65                  70                  75

ACA GCA CAA GGA GCA GCT GAA TTC AGA GAT ATA GCT ATC TTT CAA GAT           289
Thr Ala Gln Gly Ala Ala Glu Phe Arg Asp Ile Ala Ile Phe Gln Asp
                80                  85                  90

TAT CAT GGC TTG GCT GAA TTC AGA GAG GCT GTT GCA AAG TTT ATG GGG           337
Tyr His Gly Leu Ala Glu Phe Arg Glu Ala Val Ala Lys Phe Met Gly
            95                  100                 105

AAA GTG AGA AGA AAC AGA GCT TCA TTT GAC CCT GAT CGG ATT GTT ATG           385
Lys Val Arg Arg Asn Arg Ala Ser Phe Asp Pro Asp Arg Ile Val Met
        110                 115                 120

AGT GGA GGA GCA ACT GGA GCT CAT GAA ATG ATT GCT TTC TGT TTG GCT           433
Ser Gly Gly Ala Thr Gly Ala His Glu Met Ile Ala Phe Cys Leu Ala
    125                 130                 135

GAT CCT GGC GAT GCA TTC TTG GTT CCA ACT CCT TAT TAT CCA GGG TTT           481
Asp Pro Gly Asp Ala Phe Leu Val Pro Thr Pro Tyr Tyr Pro Gly Phe
140                 145                 150                 155

GAT AGA GAT TTG AGA TGG AGA ACG GGA GTC AAA CTC ATT CCA GTT GTC           529
Asp Arg Asp Leu Arg Trp Arg Thr Gly Val Lys Leu Ile Pro Val Val
                160                 165                 170
```

```
TGT GAA AGC TCA AAC GAT TAC CAG ATC ACC ATA GAA GCC CTG GAA GCT      577
Cys Glu Ser Ser Asn Asp Tyr Gln Ile Thr Ile Glu Ala Leu Glu Ala
            175                 180                 185

GCT TAT GAA ACC GCA CAA GAA GCT GAC ATC AAG GTA AAG GGT TTG CTC      625
Ala Tyr Glu Thr Ala Gln Glu Ala Asp Ile Lys Val Lys Gly Leu Leu
            190                 195                 200

ATA CCC AAC CCA TCA AAC CCA CTG GGA ACA ATT ATT ACC AAG GAC ACA      673
Ile Pro Asn Pro Ser Asn Pro Leu Gly Thr Ile Ile Thr Lys Asp Thr
        205                 210                 215

TTA GAA GCT CTA GTC ACC TTC ACC AAC CAC AAG AAC ATT CAT CTG GTG      721
Leu Glu Ala Leu Val Thr Phe Thr Asn His Lys Asn Ile His Leu Val
220                 225                 230                 235

TGT GAT GAG ATA TAT GCT GCT ACC GTC TTC AGC CAG CCC GAA TTC ACC      769
Cys Asp Glu Ile Tyr Ala Ala Thr Val Phe Ser Gln Pro Glu Phe Thr
                240                 245                 250

AGC ATA GCC GAG ATA ATT GAA GAA GAT AAA ATT TGT TGC AAT CGT GAT      817
Ser Ile Ala Glu Ile Ile Glu Glu Asp Lys Ile Cys Cys Asn Arg Asp
            255                 260                 265

CTC ATC CAC ATC ATT TAC AGT TTA TCC AAA GAC ATG GGA TTC CCT GGA      865
Leu Ile His Ile Ile Tyr Ser Leu Ser Lys Asp Met Gly Phe Pro Gly
            270                 275                 280

TTT AGA GTT GGC ATT GTG TAT TCA TAC AAT GAT GCA GTG GTG AGT TGT      913
Phe Arg Val Gly Ile Val Tyr Ser Tyr Asn Asp Ala Val Val Ser Cys
            285                 290                 295

GCT CGT AAG ATG TCG AGC TTC GGC CTA GTA TCT TCG CAA ACC CAG TAT      961
Ala Arg Lys Met Ser Ser Phe Gly Leu Val Ser Ser Gln Thr Gln Tyr
300                 305                 310                 315

CTG ATT GCA TCC ATG TTA GCA GAC GAT GAA TTT GTA GAC CAA TTT ATT     1009
Leu Ile Ala Ser Met Leu Ala Asp Asp Glu Phe Val Asp Gln Phe Ile
                320                 325                 330

GTA GAG AGC AGA AAG AGG CTG GCA ATG AGA CAT AGT TTT TTC ACA CAA     1057
Val Glu Ser Arg Lys Arg Leu Ala Met Arg His Ser Phe Phe Thr Gln
            335                 340                 345

AGA CTT GCT CAA GTA GGC ATT AAC TGT TTA AAA AGC AAT GCT GGT CTT     1105
Arg Leu Ala Gln Val Gly Ile Asn Cys Leu Lys Ser Asn Ala Gly Leu
            350                 355                 360

TTT GTG TGG ATG GAT TTG CGT AGA CTG CTG AAA GAA CAG ACA TTT GAA     1153
Phe Val Trp Met Asp Leu Arg Arg Leu Leu Lys Glu Gln Thr Phe Glu
            365                 370                 375

GCA GAA ATG GTG TTA TGG AGA GTA ATT ATA AAC GAA ATA AAA CTC AAT     1201
Ala Glu Met Val Leu Trp Arg Val Ile Ile Asn Glu Ile Lys Leu Asn
380                 385                 390                 395

GTA TCT CCT GGT TCG TCT TTC CAC TGC TCA GAA CCT GGC TGG TTC AGG     1249
Val Ser Pro Gly Ser Ser Phe His Cys Ser Glu Pro Gly Trp Phe Arg
                400                 405                 410

GTT TGC TTT GCA AAC ATG GAC GAT AAG ACA ATG GAA ATT GCA CTG TCA     1297
Val Cys Phe Ala Asn Met Asp Asp Lys Thr Met Glu Ile Ala Leu Ser
            415                 420                 425

AGA ATC AAA ACC TTC ATG CTT CAA CAT AAG GAA GCA ATG GTG CCT AAA     1345
Arg Ile Lys Thr Phe Met Leu Gln His Lys Glu Ala Met Val Pro Lys
            430                 435                 440

AAG AAA CTT TGC TGG CAA ACT AGT CTT AGA CTC AGC TTC TCC TCT CGC     1393
Lys Lys Leu Cys Trp Gln Thr Ser Leu Arg Leu Ser Phe Ser Ser Arg
        445                 450                 455

TAT GAG GAT ATC ATG GAG ACA CCG GGT TCG TTC ATG TCT CCT CAC TCG     1441
Tyr Glu Asp Ile Met Glu Thr Pro Gly Ser Phe Met Ser Pro His Ser
460                 465                 470                 475

CCT ATA CCT CAA TCA CCT CTT GTT CGA GCC AGG ACA TAGATCCAAA          1487
Pro Ile Pro Gln Ser Pro Leu Val Arg Ala Arg Thr
                480                 485
```

```
TACTTATGAT CACAACCAGT TTTCAGATGA TGATGATGAT AATATGTCGA TTCGTTGGGT      1547

GATGATTCGA GTGATCGTGC ATCAGGGCGA TCTAGTTGAC AAGTTAGCTA ATTATATTTT      1607

GATCTTGTTA GAATCATGTG TAAATAAGAG AAAGTTGGTG CATTCTTTTC CAGTTACAGA      1667

TCAATTGATC ATATTCTACT GGTTTATAAG CACACAACTA TGTTATTTA  TTTATTTTTT      1727

TAATAATTTT TTTTCACATA CAACAAGTGT AGGTGAAAAA ATATTTAAGT GTTTGTTTGT      1787

GTGCGTTGCT CAAGCACGTT ACACCTATCA TGTCTTCCTT CCTAATTATT TTATATGTCA      1847

TGATCAAGTT AATTTTATTT TAAAAAAAAA AAAAAAAAA A                          1888
```

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Val Leu Met Leu Arg Asn Gln Glu Leu Leu Ser Lys Ile Ala Thr
 1               5                  10                  15

Ser Asn Gly His Gly Glu Asp Ser Pro Tyr Phe Asp Gly Trp Lys Ala
            20                  25                  30

Tyr Asp Ser Asp Pro Phe His Pro Thr Gln Asn Pro Glu Gly Val Ile
        35                  40                  45

Gln Met Gly Leu Ala Glu Asn Gln Leu Cys Phe Asn Leu Ile His Glu
    50                  55                  60

Trp Leu Leu Lys Asn Pro Glu Ala Ser Ile Cys Thr Ala Gln Gly Ala
65                  70                  75                  80

Ala Glu Phe Arg Asp Ile Ala Ile Phe Gln Asp Tyr His Gly Leu Ala
                85                  90                  95

Glu Phe Arg Glu Ala Val Ala Lys Phe Met Gly Lys Val Arg Arg Asn
            100                 105                 110

Arg Ala Ser Phe Asp Pro Asp Arg Ile Val Met Ser Gly Gly Ala Thr
        115                 120                 125

Gly Ala His Glu Met Ile Ala Phe Cys Leu Ala Asp Pro Gly Asp Ala
    130                 135                 140

Phe Leu Val Pro Thr Pro Tyr Tyr Pro Gly Phe Asp Arg Asp Leu Arg
145                 150                 155                 160

Trp Arg Thr Gly Val Lys Leu Ile Pro Val Val Cys Glu Ser Ser Asn
                165                 170                 175

Asp Tyr Gln Ile Thr Ile Glu Ala Leu Glu Ala Ala Tyr Glu Thr Ala
            180                 185                 190

Gln Glu Ala Asp Ile Lys Val Lys Gly Leu Leu Ile Pro Asn Pro Ser
        195                 200                 205

Asn Pro Leu Gly Thr Ile Ile Thr Lys Asp Thr Leu Glu Ala Leu Val
    210                 215                 220

Thr Phe Thr Asn His Lys Asn Ile His Leu Val Cys Asp Glu Ile Tyr
225                 230                 235                 240

Ala Ala Thr Val Phe Ser Gln Pro Glu Phe Thr Ser Ile Ala Glu Ile
                245                 250                 255

Ile Glu Glu Asp Lys Ile Cys Cys Asn Arg Asp Leu Ile His Ile Ile
            260                 265                 270

Tyr Ser Leu Ser Lys Asp Met Gly Phe Pro Gly Phe Arg Val Gly Ile
        275                 280                 285
```

| | | | | | | | | | | | | | |
|---|---|---|---|---|---|---|---|---|---|---|---|---|---|
| Val | Tyr 290 | Ser | Tyr | Asn | Asp 295 | Ala | Val | Val | Ser | Cys 300 | Ala | Arg | Lys | Met | Ser |
| Ser 305 | Phe | Gly | Leu | Val | Ser 310 | Ser | Gln | Thr | Gln | Tyr 315 | Leu | Ile | Ala | Ser | Met 320 |
| Leu | Ala | Asp | Asp | Glu 325 | Phe | Val | Asp | Gln | Phe 330 | Ile | Val | Glu | Ser | Arg 335 | Lys |
| Arg | Leu | Ala | Met 340 | Arg | His | Ser | Phe | Phe 345 | Thr | Gln | Arg | Leu | Ala 350 | Gln | Val |
| Gly | Ile | Asn 355 | Cys | Leu | Lys | Ser | Asn 360 | Ala | Gly | Leu | Phe | Val 365 | Trp | Met | Asp |
| Leu | Arg 370 | Arg | Leu | Leu | Lys | Glu 375 | Gln | Thr | Phe | Glu | Ala 380 | Glu | Met | Val | Leu |
| Trp 385 | Arg | Val | Ile | Ile | Asn 390 | Glu | Ile | Lys | Leu | Asn 395 | Val | Ser | Pro | Gly | Ser 400 |
| Ser | Phe | His | Cys | Ser 405 | Glu | Pro | Gly | Trp | Phe 410 | Arg | Val | Cys | Phe | Ala 415 | Asn |
| Met | Asp | Asp | Lys 420 | Thr | Met | Glu | Ile | Ala 425 | Leu | Ser | Arg | Ile | Lys 430 | Thr | Phe |
| Met | Leu | Gln 435 | His | Lys | Glu | Ala | Met 440 | Val | Pro | Lys | Lys | Lys 445 | Leu | Cys | Trp |
| Gln | Thr 450 | Ser | Leu | Arg | Leu | Ser 455 | Phe | Ser | Ser | Arg | Tyr 460 | Glu | Asp | Ile | Met |
| Glu 465 | Thr | Pro | Gly | Ser | Phe 470 | Met | Ser | Pro | His | Ser 475 | Pro | Ile | Pro | Gln | Ser 480 |
| Pro | Leu | Val | Arg | Ala 485 | Arg | Thr | | | | | | | | | |

( 2 ) INFORMATION FOR SEQ ID NO:3:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAGAGAGAGA GAGAGAGAGA ACTAGTCTCG AGTTTTTTTT TTTTTTTTTT    50

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AATTCGGCAC GAG    13

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCCGAATTCA TGGGACTTGC GAAGAATCCA                                                                    30

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TTTCCAGAGA CTTATCCATC GGTCATCT                                                                      28

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GCCAAGCTTC CAGTGAGTAA GTCTCTGAGA A                                                                  31

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGAGTTAGTC GAGGAGTTGT GCA                                                                           23

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CCCATGGGAA GAAGACCTCA ATGATCTTT                                                                     29

( 2 ) INFORMATION FOR SEQ ID NO:10:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

ATAGTTATGG CGAAAGACAA CACTGTCGCG TAGACCATGA ATTCAGCTGC TCCTTGTCC                                    59

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
TAATACGACT CACTATAGGG                                                20
```

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
AATTAACCCT CACTAAAGGG                                                20
```

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
TGAATTCAGC TGCTCCTTGT CT                                             22
```

( 2 ) INFORMATION FOR SEQ ID NO:14:

( i ) SEQUENCE CHARACTERISTICS:
        ( A ) LENGTH: 1620 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

```
AAGCTTATGG AGAACTTCCC AATTATTAAC TTGGAAAAGC TCAATGGAGA TGAGAGAGCC     60
AACACCATGG AAATGATCAA AGATGCTTGT GAGAATTGGG GCTTCTTTGA GGTAATCATA    120
AATTACATAA ACATATTAAT ATGTTTGTTT CAATTTATCA GTCATACTTT TCTCTGTTTT    180
AAAATTAATG TCACTTTCAA TATTTAATAA TTCGCATGAC ATGTTTATAA CACAACAAGA    240
TATAGGTTAC ATTTTGATAC ATTATATATA ACTTCTGTCA CACGACTCAA AAGTCTTTCT    300
TAATTTCTTG AATTCAATGA TCGATCAAAC TAAGACACGT AAAATGAAAC GGGGAATAGT    360
AATTCTGTTT GCTTATGTGA TCATTGTAGT TGGTGAACCA TGGAATTCCA CATGAAGTAA    420
TGGACACAGT AGAGAAAATG ACAAAGGGAC ATTACAAGAA GTGCATGGAA CAGAGGTTTA    480
AGGAACTAGT GGCAAGTAAG GGACTTGAGG CTGTTCAAGC TGAGGTTACT GATTTAGATT    540
GGGAAAGCAC TTTCTTCTTG CGCCATCTTC CTACTTCTAA TATCTCTCAA GTACCCGATC    600
TTGACGAAGA ATACAGGTAC ATACATGTGT CCTACATATT GCGTATATAA TAAATAAACA    660
```

-continued

| | | | | | |
|---|---|---|---|---|---|
| CAAAATTTAA | GTTATATACG | CTGACAGTAT | AACTAATTAT | AATGTTGTAC | CAAATGATGC | 720
| AGAGAGGTGA | TGAGAGATTT | TGCTAAAAGA | TTGGAGAAAT | TGGCTGAGGA | GTTACTTGAC | 780
| TTACTCTGTG | AAAATCTTGG | ACTTGAAAAA | GGTTACTTGA | AAAATGCCTT | TTATGGATCA | 840
| AAAGGTCCCA | ACTTTGGTAC | TAAAGTTAGC | AACTATCCAC | CATGTCCTAA | GCCCGATTTG | 900
| ATCAAGGGAC | TCCGCGCTCA | TACAGACGCA | GGAGGCATCA | TACTTCTGTT | CCAAGATGAC | 960
| AAAGTGAGTG | GCCTTCAACT | CCTCAAAGAC | GAGCAATGGA | TCGATGTTCC | TCCCATGCGC | 1020
| CACTCTATTG | TGGTTAACCT | TGGTGACCAA | CTTGAGGTAC | AAGATTCACT | AAGTGTGTGT | 1080
| GTTTTTATCA | CTATAACTTA | GAAGTAGTAA | CTAAAAATGG | TATTAATGAA | ATGTTATAAA | 1140
| AACAGGTGAT | CACTAACGGG | AAGTACAAGA | GTGTGCTGCA | CAGAGTAATT | GCACAAACAG | 1200
| ACGGGACACG | AATGTCATTA | GCCTCATTTT | ACAATCCAGG | AAGTGATGCA | GTAATATATC | 1260
| CAGCAAAAAC | TTTGGTTGAA | AAAGAGGCAG | AGGAAAGTAC | ACAAGTGTAT | CCAAAGTTTG | 1320
| TGTTTGATGA | TTACATGAAG | TTATATGCTG | GACTCAAGTT | TCAAGCCAAA | GAGCCAAGAT | 1380
| TTGAAGCAAT | GAAGGCAATG | GAAAGTGATC | CAATTGCAAG | TGCTTAGATC | CCAATTCAAT | 1440
| TAAAAAAATT | GGTGTTTGAA | AAATATATTT | AAATATAGCA | ATCTATGTAT | ACACATTATT | 1500
| TGCTCTTCTT | ATGTATGGTA | GAATAAAGTT | AGTATTAAAA | AAGATTGTGA | TTTGCTGCAT | 1560
| ATGTATCAAA | AAGAGTCCTA | ATATTTGTAT | CTATAAATAA | GGTGCCTTCT | AGTGACTCTA | 1620

( 2 ) INFORMATION FOR SEQ ID NO:15:

( i ) SEQUENCE CHARACTERISTICS:
    ( A ) LENGTH: 1035 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:15:

| | | | | | |
|---|---|---|---|---|---|
| ATTCACATCA | TATAATTTAA | TTACCAAGAA | AAATTAAGAT | GGAGAACTTC | CCAATTATCA | 60
| ACTTGGAAAA | TCTTAATGGA | GATGAGAGAG | CCAAAACCAT | GGAAATGATC | AAAGATGCAT | 120
| GTGAGAATTG | GGGCTTCTTT | GAGTTGGTGA | ACCATGGGAT | TCCACATGAA | GTAATGGACA | 180
| CTGTGGAGAA | ATTGACAAAG | GGACATTACA | AGAAGTGCAT | GGAACAGAGG | TTTAAGGAAT | 240
| TGGTAGCAAG | TAAGGGACTT | GAAGCTGTGC | AAGCTGAGGT | TACTGATTTA | GATTGGGAAA | 300
| GCACTTTCTT | CTTGCGCCAT | CTTCCTACTT | CTAATATCTC | TCAAGTACCC | GATCTTGACG | 360
| AAGAATACAG | AGAGGTGATG | AGAGATTTTG | CTAAAAGATT | GGAGAAGTTG | GCTGAGGAGT | 420
| TACTTGACTT | ACTCTGTGAA | AATCTTGGAC | TTGAAAAAGG | TTATTTGAAA | AATGCCTTTT | 480
| ATGGATCAAA | AGGTCCCAAT | TTCGGTACTA | AAGTTAGCAA | CTATCCACCA | TGTCCTAAGC | 540
| CCGATTTGAT | CAAGGGACTC | CGCGCTCATA | CAGACGCAGG | AGGCATCATA | CTTCTGTTCC | 600
| AAGATGACAA | AGTGAGTGGC | CTTCAACTCC | TCAAAGACGA | GCAATGGATC | GATGTTCCTC | 660
| CCATGCGCCA | CTCTATTGTG | GTTAACCTTG | GTGACCAGCT | TGAGGTGATT | ACCAACGGGA | 720
| AGTACAAGAG | CGTGATGCAC | AGAGTGATTG | CACAAACAGA | TGGGACTCGG | ATGTCACTAG | 780
| CATCATTTTA | TAATCCAGGA | AATGACGCGG | TGATCTATCC | AGCACCATCT | CTAATTGAGG | 840
| AAAGCAAGCA | AGTTTATCCG | AAATTCGTGT | TTGATGATTA | CATGAAGTTA | TATGCTGGAC | 900
| TAAAGTTTCA | GCCAAAAGAG | CCAAGATTTG | AAGCAATGAA | GGCTATGGAA | GCTAATGTGG | 960
| AATTAGTTGA | TCAAATTGCA | AGTGCTTAAA | GAAAATTATT | ATGTTCTTGG | AAGTTATACA | 1020
| AACGTAGCTA | ATTAA | | | | | 1035

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GCCTCACTAC GACTGCGGGG         20

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TCATGCTGTG CAGATGGGTT C         21

( 2 ) INFORMATION FOR SEQ ID NO:18:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AGCTATAACT TCGTATAGCA TACATTATAC GAAGTTAT         38

( 2 ) INFORMATION FOR SEQ ID NO:19:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

AGCTATAACT TCGTATAATG TATGCTATAC GAAGTTAT         38

( 2 ) INFORMATION FOR SEQ ID NO:20:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

ATAACTTCGT ATAGCATACA TTATACGAAG TTATAGCT         38

NUCLEIC ACIDS ENCODING A PAPAYA ACC SYNTHASE GENE

FIELD OF THE INVENTION

The present invention relates to methods for isolating the papaya 1-aminocyclopropane-1-carboxylic acid synthase (ACC synthase) gene, using it in conjunction with general plant regulatory sequences both 5' to and 3' to this gene and modifying ethylene biosynthesis and hence fruit ripening in papaya plants.

BACKGROUND OF THE INVENTION

Many fruits, such as papayas comprise important tropical fruit crops. For example, the increasing popularity of papaya has led to its spread from its countries of origin in South and Central America to countries throughout the tropics. Unfortunately, its extreme sensitivity to cold makes papaya impossible to produce in temperate and even sub-tropical regions. However, while production is in the tropics, the major markets are in temperate regions, necessitating considerable transportation time to reach market. Because of its ripening characteristics, papaya fruits have a short postharvest shelf-life and must be marketed as soon as possible. Reduced temperature storage can extend the postharvest life somewhat. However, their extreme sensitivity to chilling injury limits the time and temperature to which papaya fruit can be chilled and still ripen. Nonetheless, consumer demand mandates that fresh, suitably ripe fruit be available.

Ripening of Fruits

Ripening involves a number of changes in fruit. In fleshy fruits, chlorophyll is degraded and other pigments often form, changing the color of the fruit. Simultaneously, the fleshy part softens as a result of the enzymatic digestion of pectin, the principal component of the middle lamella of the cell wall, and starches and organic acids are metabolized into sugars. Fruits are divided into two major groups, based on the respiratory behavior observed during the ripening process. In the climacteric fruits, such as tomatoes, avocadoes, bananas, apples and pears (i.e., pome fruits), and papaya, there is a burst of respiration (i.e., a large increase in oxygen uptake termed the "climacteric rise") accompanied by marked changes in fruit composition and texture. Fruits that show a steady decline or gradual ripening are called "non-climacteric fruits" (e.g., citrus fruits, grapes, and strawberries). In contrast to the climacteric fruits, these fruits show no changes in fruit composition.

Role of Ethylene in Fruit Development and Ripening

In climacteric fruits, a marked increase in ethylene production is concomitantly observed with this respiratory upsurge. Ethylene has long been recognized in botanical history. The first observations were made in the 1800's, when it was found that shade trees along the city streets were becoming defoliated due to the escape of ethylene gas from the gas mains used for illuminating lamps (P. Raven et al., *Biology of Plants*, 5th ed., Worth Publishers, 1992, p. 554). Ethylene has major impacts on agriculture in abscission, seed germination, leaf and flower senescence, and fruit ripening (Theologis, Cell 70: 181–184 [1992]). Ethylene is used commercially to promote loosening of fruit such as cherries, blackberries, grapes, and blueberries, thereby facilitating mechanical harvesting of fruit crops.

Ethylene plays an important regulatory role in the ripening of climacteric fruits [Yang and Hoffman, Ann. Rev. Physiol., 35: 155 (1984); Abeles et al., *Ethylene in Plant Biology*, 2nd Ed., Academic Press, New York, p. 414 (1992)]. Papaya is a climacteric fruit [Wardlaw, Tropical Agriculture, 24: 288 (1936); Jones and Kubota, Plant Physiol., 15: 711 (1940); Akamine and Goo, Hort. Science, 14: 138 (1979); Paull and Chen, Plant Physiol., 72: 382 (1983)]. Ethylene in concentrations as little as 1 parts per million in the ambient atmosphere will hasten the onset of the climacteric (Raven et al., p.554, supra). However, ethylene is also produced biosynthetically, in amounts ranging from almost none, to up to 500 nl/g per hour (Burg, Ann. Rev. Plant Physiol., 13: 265–302 [1962]).

Exposure to ethylene during storage and transport has a major impact on the quality of fruit sold. Techniques to avoid exposure of fruits to ethylene until just before marketing have been used to control and regulate the timing of the ripening process. For example, tomatoes are often picked when they are green, and then stored in the absence of ethylene until just before marketing. Ventilation of the fruit with air under hyperbaric pressures have been used (Burg and Burg, Science 153: 314–315 [1966]). This accelerates the escape of environmental ethylene, and the reduced oxygen tension reduces the sensitivity of the fruit to ethylene. Also, various inhibitors of ethylene action have been used to reduce the effects of ethylene on harvested fruit, including silver ions and carbon dioxide (Yang and Hoffman, Ann. Rev. Plant Physiol., 35:155 [1984]). Unfortunately, these approaches are expensive, may be toxic, and are far less than satisfactory or even adequate.

In climacteric fruit, such as papaya, there is a rapid rise in respiration and in ethylene biosynthesis just prior to the final stages of fruit ripening when softening and development of color and flavor occurs. It appears that ethylene regulates fruit ripening by coordinating the expression of genes responsible for the respiratory rise, autocatalytic ethylene production, degradation of chlorophyll, synthesis of carotenoid lycopene, conversion of starch to sugars, and increased activity of cell wall-degrading enzymes (see e.g., Gray et al., Plant Mol. Biol., 19: 69–87 [1992]; and Theologis et al., in J. C. Pech et al., (eds.) *Cellular and Molecular Aspects of Plant Hormone Ethylene*, [1993], pp. 19–23).

The biosynthesis of ethylene begins with the reaction of methionine and ATP to form S-adenosylmethionine ("SAM"). ACC synthase converts s-adenosylmethionine to 1-aminocyclopropane-1-carboxylic acid (ACC) which is oxidized to give ethylene by aminocyclopropane-1-carboxylic acid oxidase (ACC oxidase) [Yang and Hoffman, supra]. ACC (i.e., the acid) formation is affected by various conditions that stimulate ethylene production (e.g., high auxin concentrations, air pollution damage, anaerobiosis, drought, chilling, viral infection, cadmium and lithium, and the physical wounding of the plant). ACC synthase, the first enzyme in the pathway of ethylene production appears to be the rate limiting step. ACC synthase is present in an extremely low amount and is labile [Yang and Hoffman, supra]. Because of its scarcity and lability, purification of the ACC synthase enzyme has proven quite difficult but has now been achieved, at least partially, for a number of higher plant species [Imaseki, in *The Plant Hormone Ethylene*, Matto and Suttle (eds.), CRC Press, Inc. Boca Raton, pp. 1–20 (1991); Kende, Ann. Rev. Plant Physiol., 44: 283 (1993)]. Inhibition of ethylene biosynthesis by chemical (e.g., silver or carbon dioxide) or biotechnological means (Oeller et al., Science 254: 437 [1991]) inhibits the final stages of ripening. However, due to problems with toxicity, chemical inhibition of ripening is not employed in commercial settings. Although naturally-occurring ripening tomato mutants exist, their phenotype is not reversible by exposure to ethylene.

Recombinant DNA technology that has been used to isolate a number of ACC synthase genes as shown in Table 1 below. Table 1 gives a listing of plant ACC synthase sequences available in the GenBank electronic database. However, with the exception of the apple and a subset of the tomato ACC synthase gene sequences, none of these ACC synthase genes are involved with the ripening of fruit.

TABLE 1

ACC Synthase Sequences From Various Plants

| Plant Species | Locus Name[1] | Size[2] | Type[3] |
|---|---|---|---|
| Moth orchid | DORAMICAR | 1552 | mRNA |
| (Doritaenopsis sp.) | DORAMICAR | 1615 | mRNA |
| Rice | RICACC1A | 1485 | mRNA |
| (Oryza sativa) | RICACCIB | 2778 | DNA |
| Carnation | DCACCS | 1116 | RNA |
| (Dianthus caryophyllus) | DCAMCRBSY | 1814 | RNA |
|  | DINCARACC | 1942 | mRNA |
| Petunia | PHAMCRBSY | 1746 | mRNA |
| (Petunia hybrida) |  |  |  |
| Arabidopsis (Arabidopsis | ATACCSYNM | 159 | mRNA |
| thaliana) | ATACCSYNG | 5613 | DNA |
|  | ATHACSC | 1491 | mRNA |
|  | ATHACS | 4880 | DNA |
| Winter squash | CUCACCSYN | 1703 | mRNA |
| (Cucurbita maxima) | CUCACCW | 1699 | mRNA |
|  | CUCACCA | 1638 | mRNA |
| Zucchini | CUCACC1 | 16646 | DNA |
| (Cucurbita pepo) | TOMRNA | 268 | RNA |
|  | TOMRNAB | 271 | RNA |
|  | TOMRNAC | 271 | RNA |
| Tomato (Lycopersicon | TOMRNAD | 219 | RNA |
| esculentum) | TOMACT | 420 | mRNA |
|  | TOMACS | 1819 | mRNA |
|  | LEAC | 1529 | mRNA |
| Tomato (Lycopersicon | TOMACCS | 1635 | mRNA |
| esculentum) | LEACC4MR | 1616 | RNA |
|  | LEACC2MR | 1775 | RNA |
|  | LEACC2G | 7244 | DNA |
|  | TOMACS4A | 5449 | DNA |
| Tobacco | NTXACCSYN | 1751 | RNA |
| (Nicotiana tabacum) |  |  |  |
| Mung bean | VIRACCSY01 | 296 | DNA |
| (Vigna radiata) | VIRACCSY02 | 309 | DNA |
|  | VIRACCSY03 | 314 | DNA |
|  | VRACCSYN | 1104 | RNA |
|  | VRACCSYNM | 1923 | RNA |
|  | VIRACCSYNT | 1393 | DNA |
| Soybean | GMCACCS1 | 1789 | RNA |
| (Glycine max) |  |  |  |
| Apple | MSU03294 | 1618 | mRNA |
| (Malus sylvestris) |  |  |  |

Note:
1 = locus as in GenBank; 2 = includes both coding and non-coding sequences; 3 = genomic (DNA) or cDNA (RNA) clones.

Probing of genomic DNA with these sequences revealed that ACC synthase is encoded by a highly divergent multigene family (for a review, see e.g., Theologis et al., Develop. Genet., 14: 282–295 [1993]). Not all of the ACC synthase genes present in a given plant are active in response to fruit ripening. Some of the ACC synthetase genes respond to other stimuli, generally biotic stress. Thus, a subset of the ACC synthase genes will be turned on (i.e., transcriptionally activated) in response to ripening. For example, in tomatoes, ACC synthase is encoded by at least six divergent genes, only two of which are expressed during fruit ripening. In rice and Arabidopsis, different ACC synthase genes are expressed in response to developmental, hormonal and environmental stimuli.

Recombinant DNA technology (e.g., antisense technology) has been used to alter fruit ripening in tomatoes (Oeller et al., Science 254: 437 [1991]). To alter the ripening of tomatoes, the 35S promoter of the cauliflower mosaic virus was used to drive expression of an antisense ACC synthase cDNA isolated from tomato fruit. Transgenic plants were obtained that produced very low levels of ethylene (<0.1 nl/g per hour), and ripened slowly or not at all. The transgenic plants having the highest levels of inhibition of ACC synthase activity synthesized very low levels of ethylene and the fruit remained green, did not soften and did not develop the aroma of ripe tomato. These fruit ripened normally when provided with exogenous ethylene.

While the regulation of ripening in tomatoes has been achieved by the inhibition of ACC synthase using recombinant DNA technology, there are no reports of inhibition of ripening in tropical fruits using recombinant DNA technology.

Worldwide, billions of dollars are lost associated with the effect of ethylene on plant ripening and spoilage due to fruit ripening too soon before marketing and consumer rejection of over-ripe fruit. The effects in developing countries are even more significant due to the lack of sufficient refrigeration and transportation capabilities. What is needed is better control of ripening for a variety of commercially important climacteric fruit species.

SUMMARY OF THE INVENTION

The present invention describes the isolation of a papaya fruit-specific ACC synthase cDNA and use of this gene in co-suppression and/or antisense to regulate ripening in papaya fruit. Use of this gene in conjunction with ACC oxidase in a heterologous organism, such as yeast, to produce exogenous ethylene on demand to affect ripening of fruit.

One embodiment of the present invention comprises a purified oligonucleotide comprising the nucleotide sequence set forth in SEQ ID NO:1. In a preferred embodiment, the oligonucleotide further comprises 5' and 3' flanking regions. In an alternative embodiment, the oligonucleotide further comprises intervening regions. In yet another preferred embodiment, the oligonucleotide further comprises recombinant DNA vector sequences.

In another embodiment, the present invention comprises a method for inhibiting ripening of papaya comprising the steps of: providing a purified oligonucleotide comprising the nucleic acid sequence set forth in SEQ ID NO. 1, and at least one papaya plant cell, and introducing the oligonucleotide into the papaya plant cell under conditions such that ripening is inhibited. In one embodiment, the oligonucleotide is extrachromosomal in the papaya plant cell. In an alternative embodiment, the oligonucleotide is integrated into the genome of the papaya plant cell under conditions such that the plant cell is transformed. In a preferred embodiment, the oligonucleotide is linked to a promoter. In another preferred embodiment, the oligonucleotide is linked to the promoter under conditions such that ACC synthase transcripts are produced. In another embodiment, the oligonucleotide is linked to the promoter such that antisense ACC synthase transcripts are produced.

In an alternative embodiment, the present invention comprises a method for ripening fruit comprising the steps of providing an unripe fruit and a recombinant host cell wherein the host cell is capable of producing and releasing exogenous ethylene, and exposing the unripe fruit to the recombinant host cell under conditions such that the unripe fruit ripens. In one embodiment, the recombinant host cell comprises the nucleic acid sequences encoding ACC synthase and ACC oxidase. In a particularly preferred embodiment, the nucleic acid sequence comprises two or more nucleic acids selected from the group consisting of SEQ ID NOS: 1, 14, and 15. In one embodiment of the method, the host cell is provided in a re-hydratable form. In another preferred embodiment, the recombinant host cell is a eukaryote. In another embodiment, the eukaryotic host cell is a yeast. In yet another embodiment, the host cell is a member of the genus Saccharomyces. In a particularly preferred embodiment, the unripe fruit is a climacteric fruit, including, but not limited to papayas.

In yet another embodiment, the present invention comprises a method for ripening fruit comprising the steps of providing an unripe fruit and a recombinant host cell wherein the host cell is capable of expressing ACC synthase and ACC oxidase to produce and release ethylene into the environment, growth medium, and liquid; exposing the growth medium to the liquid under conditions such that the host cell is capable of growth; and exposing the unripe fruit to the recombinant host cell under conditions such that the unripe fruit ripens. In one embodiment, the recombinant host cell comprises the nucleic acid sequences encoding ACC synthase and ACC oxidase. In a preferred embodiment, the recombinant host cell comprises pAY41 and pYE13. In another preferred embodiment, the nucleic acid sequences present in the recombinant host cell are selected from the group comprising SEQ ID NOS: 1, 14, and 15. In another embodiment, the recombinant host cell comprises the nucleic acid sequences purified and isolated from papaya.

It is contemplated that the recombinant host cell will be a eukaryote, including but not limited to plants such as fruits, fungi such as yeasts (e.g., Saccharomyces), molds, and mushrooms, as well as other eukaryotic organisms.

It is contemplated that the method of the present invention will be used with unripe fruit that are climacteric fruits, including but not limited to papayas.

The present invention also comprises a method for ripening fruit comprising the steps of providing an unripe fruit and a recombinant host cell wherein the host cell is capable of expressing ACC synthase and ACC oxidase to produce and release ethylene into the environment, growth medium, liquid, and a container; placing the unripe fruit, recombinant host cell, growth medium and liquid into the container; exposing the growth medium to the liquid under conditions such that the host cell is capable of growth; and exposing the unripe fruit to the recombinant host cell under conditions such that the unripe fruit ripens. It is contemplated that the recombinant host cell comprises the nucleic acid sequences encoding ACC synthase and ACC oxidase. It is also contemplated that the recombinant host cell will comprise the pAY41 and pYE13. It is particularly contemplated that the nucleic acid sequences of the recombinant host cell are selected from the group comprising SEQ ID NOS: 1, 14 and 15. In a particularly preferred embodiment, the recombinant host cell comprises the nucleic acid sequences purified and isolated from papaya.

As with the previous embodiments, it is contemplated that the recombinant host cell will be a eukaryote, including but not limited to plants such as fruits, fungi such as yeasts (e.g., Saccharomyces), molds, and mushrooms, as well as other eukaryotic organisms. It is further contemplated that this method of the present invention will be used with unripe fruit that are climacteric fruits, including but not limited to papayas.

DESCRIPTION OF THE DRAWINGS

FIG. 1 depicts the nucleotide sequence of the papaya ACC synthase cDNA (SEQ ID NO:1).

FIG. 2 shows the direction of extension and the sequence of six degenerate primers homologous to the four highly conserved regions of a consensus ACC synthase sequence.

DEFINITIONS

Figure 3:
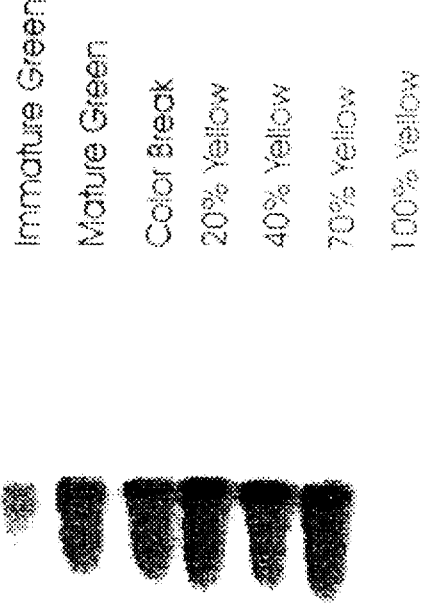
FIG. 3 depicts a Northern blot showing the expression of the papaya ACC synthase mRNA in ripening papaya fruit.

To facilitate understanding of the invention, a number of terms are defined below.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a promoter which permits the synthesis of a coding strand. Once introduced into a host cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "transgene" refers to a gene which is introduced into a plant. The transgene may comprise plant gene sequences which comprise cDNA forms of a plant gene; the cDNA sequences may be expressed in either a sense (to produce mRNA) or anti-sense orientation (to produce an anti-sense RNA transcript which is complementary to the mRNA transcript). Transgenes are distinguished from endogenous plant genes in that the transgene sequences are typically joined to DNA sequences comprising regulatory elements such as promoters which are not found naturally associated with the plant gene sequences in the chromosome. Transgenes may also comprise foreign genes (i.e., a gene(s) which is not naturally found in the plant).

As used herein the term "transgenic" when used in reference to a plant or fruit (i.e., a "transgenic plant" or "transgenic fruit") refers to a plant or fruit which contains a transgene in its cells.

As used herein, the term "polyA+RNA" refers to RNA molecules having a stretch of adenine nucleotides at the 3' end. This polyadenine stretch is also referred to as a "poly-A tail". Eukaryotic mRNA molecules contain poly-A tails and are referred to as polyA$^+$ RNA.

As used herein, the terms "cell," "cell line," and cell culture" are used interchangeably and all such designations include progeny. The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "selectable marker" refers to the use of a gene which encodes an enzymatic activity that confers the ability to grow in medium lacking what would otherwise be an essential nutrient (e.g. the URA3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with $tk^-$ cell lines, the CAD gene which is used in conjunction with CAD-deficient cells and the mammalian hypoxanthine-guanine phosphoribosyl transferase (hprt) gene which is used in conjunction with $hprt^-$ cell lines. A review of the use of selectable markers in mammalian cell lines is provided in Sambrook. J. et al., *Molecular Cloning. A Laboratory Manual*, 2nd ed., Cold Spring Harbor Laboratory Press, N.Y. (1989) pp.16.9–16.15.

As used herein, the term "vector" is used in reference to nucleic acid molecules that transfer DNA segment(s) from one cell to another. The term "vehicle" is sometimes used interchangeably with "vector."

The terms "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5X SSPE (43.8 g/l NaCl, 6.9 g/l $NaH_2PO_4 \cdot H_2O$ and 1.85 g/l EDTA, pH adjusted to 7.4 with NaOH), 0.1% SDS, 5X Denhardt's reagent [50X Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5X SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

An oligonucleotide sequence which is "substantially homologous to the papaya fruit-specific gene of SEQ ID NO:1" is defined herein as an oligonucleotide sequence which exhibits greater than or equal to 75% identity to the sequence of SEQ ID NO:1 when sequences having a length of 100 bp or larger are compared.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1M NaCl (see e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase [D. L. Kacian et al., *Proc. Natl. Acad. Sci USA* 69: 3038 (1972)]. Other nucleic acid will not be replicated by this amplification enzyme. Similarly, in the case of T7 RNA polymerase, this amplification enzyme has a stringent specificity for its own promoters [M. Chamberlin et al., *Nature* 228: 227 (1970)]. In the case of T4 DNA ligase, the enzyme will not ligate the two oligonucleotides where there is a mismatch between the oligonucleotide substrate and the template at the ligation junction [D. Y. Wu and R. B. Wallace, *Genomics* 4: 560 (1989)]. Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences [*PCR Technology*, H. A. Erlich (ed.) (Stockton Press 1989)].

As used herein, the terms "PCR product", "PCR fragment" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eucaryotes comprise "promoter" and "enhancer" elements. Promoters and enhancers consist of short arrays of DNA sequences that interact specifically with cellular proteins involved in transcription [Maniatis, T. et al., *Science* 236: 1237 (1987)]. Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest. A wide variety of promoters have been isolated from plants, which are functional not only in the cellular source of the promoter, but also in numerous other plant species. There are also other promoters, e.g., viral and Ti-plasmid which can be used. These promoters include promoters from the Ti-plasmid, such as the octopine synthase promoter, the nopaline synthase promoter, the mannopine synthase promoter, promoters from other open reading frames in the T-DNA, such as ORF7, etc. Promoters isolated from plant viruses include the 35S promoter from cauliflower mosaic virus (CaMV). Promoters which have been isolated and reported for plants include ribulose-1,3-biphosphate carboxylase small subunit promoter, phaseolin promoter, etc.

The presence of "splicing signals" on an expression vector often results in higher levels of expression of the recombinant transcript. Splicing signals mediate the removal of introns from the primary RNA transcript and consist of a splice donor and acceptor site [Sambrook, J. et al., *Molecular Cloning: A Laboratory Manual*, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene.

The term "transfection" or "transfected" refers to the introduction of foreign DNA into a cell.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists [J. Sambrook et al. (1989) *Molecular Cloning: A Laboratory Manual,* Cold Spring Harbor Press, N.Y., pp 9.31–9.58].

The term "Northern Blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists [J. Sambrook, J. et al. (1989) supra, pp 7.39–7.52].

The term "prototrophic" or "prototrophy" refers to an organism that can survive growth under conditions where one or more essential nutrients are lacking in the growth medium. For example, if a yeast cell is transformed to uracil prototrophy, this means that the yeast cell now contains gene sequences encoding the enzyme necessary for the production of the amino acid uracil; therefore, the transformed yeast cell does not require the presence of uracil in the growth medium.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a papaya ACC synthase protein includes, by way of example, such nucleic acid in cells ordinarily expressing a papaya ACC synthase protein where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

As used herein the term "coding region" when used in reference to structural gene refers to the nucleotide sequences which encode the amino acids found in the nascent polypeptide as a result of translation of a mRNA molecule. The coding region is bounded, in eucaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and the including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences; these sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

As used herein, the term "purified" or "to purify" refers to the removal of contaminants from a sample. For example, recombinant papaya ACC synthase polypeptides are expressed in yeast host cells and the papaya ACC synthase polypeptides are purified by the removal of host cell proteins; the percent of recombinant papaya ACC synthase polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "papaya fruit-specific" when used in reference to oligonucleotide or gene sequences means that the gene sequences are expressed in the fruit of a plant; it is not required that these gene sequences be expressed only in fruit tissue. The papaya fruit-specific gene sequences will be expressed in papaya fruit tissue in a manner consistent with a role in ripening.

The terms "papaya fruit" or "papaya fruit tissue" means any tissue comprising the developing and the mature papaya fruit.

The term "papaya plant cell" refers to a cell derived from any portion of a papaya plant including but not limited to papaya fruit tissues.

The term "exogenous" when used in reference to a supply of ethylene means that the ethylene is not produced by a climacteric fruit. For example, the present invention provides genetically engineered host cells which produce ethylene; these engineered host cells are used as an exogenous source of ethylene to permit the ripening of fruit which are inhibited in the production of their own "endogenous" ethylene.

DESCRIPTION OF THE INVENTION

Novel nucleic acid compositions and constructs encoding a papaya fruit-specific ACC synthase cDNA are provided. These compositions and constructs can be used to control the expression of ACC synthase in papaya fruit. When the ACC synthase gene is placed on an expression construct in the same transcriptional orientation relative to a promoter active in plant cells, ACC synthase is produced. When the gene is placed in the opposite orientation relative to a suitable promoter, antisense sequences are produced which inhibit the expression of ACC synthase thereby inhibiting ripening. Constructs containing ACC synthase gene sequences can be reintroduced into papaya plant cells by a variety of techniques including particle bombardment [Fitch et al., Plant Cell Rep. 9: 189 (1990)] or Agrobacterium-mediated transformation [Fitch et al., Plant Cell Tiss. Org. Cult. 32: 205 (1993)]. When reintroduced with an active promoter, such as the 35S promoter of CaMV, this sequence can suppress ethylene biosynthesis by co-suppression [Napoli et al., Plant Cell. 2: 279 (1990)] or by antisense inhibition [Oeller et al., Science 254: 437 (1991)]. The papaya ACC synthase cDNA sequences of the present invention permit the isolation of the gene from genomic DNA.

The sequence of the papaya fruit-specific ACC synthase gene of the present invention is depicted in FIG. 1 and in SEQ ID NO: 1. The sequence may be used in a variety of ways. Fragments of the sequence of at least about 10 bp, more usually at least about 15 bp, and up to and including the entire (i.e., full-length) can be used as probes for the detection of complementary genomic DNA, for use in providing antisense sequences for inhibiting the expression of ACC synthase in plant cells, for use in providing co-suppression sequences and for use in directing the synthesis of active ACC synthase enzyme.

The description of the invention is divided into: I. Antisense Inhibition of Gene Expression, II. Co-suppression of Gene Expression, III. Isolation of Papaya Fruit-Specific ACC Synthase Genes, IV. Expression of Papaya ACC Synthase Gene Sequences and V. Production Of Ethylene By Genetically Engineered Host Cells to Permit Ripening of Transgenic Fruit.

I. Antisense Inhibition of Gene Expression

Antisense RNA transcripts have been used to suppress the expression of genes in eukaryotic organisms including plants. Suppression of gene expression in plants has been reported for several genes including the tomato polygalacturonase gene [Smith et al., Nature 334: 724 (1988) and U.S. Pat. No. 5, 107,065, the disclosure of which is herein incorporated by reference]; the tomato ACC synthase gene, LE-ACS2 [Oeller et al., Science 254: 437 (1991); the Brassica stearoyl-acyl-carrier protein desaturase gene [Knutzon, D. S., et al., Proc. Natl. Acad. Sci. USA 89: 2624–2628 (1992)]; the petunia chalcone synthase gene [van der Krol, A. R., et al., Nature 333: 866–869 (1988)]; the potato granule-bound starch synthase gene [Visser, R. G. F., et al., Mole. and Gen. Gene. 225: 289–296 (1991)]; and the tomato pectin methylesterase gene [Tieman, D. M., et al., Plant Cell 4: 667–679 (1992)].

To produce an antisense RNA transcript, gene sequences derived from the gene whose expression is to be reduced are placed downstream of a promoter in the opposite transcriptional orientation (relative to the direction of transcription of the endogenous gene present in the chromosome). The resulting antisense construct is introduced into the plant cell host where the antisense construct directs the transcription of antisense RNA transcripts. The antisense RNA transcript is complementary to the sense transcript produced by the endogenous gene in the plant. While not limiting the invention to any particular theory, it is believed that the antisense transcripts form a duplex with the sense transcripts thereby preventing the splicing, transcription or translation of the sense (or endogenous RNA) transcript. In this manner, a reduction in the functioning of the naturally existing RNA is achieved.

II. Co-suppression of Gene Expression

Inhibition or suppression of gene expression in plants can be achieved by the introduction of transgenes which direct the expression of sense transcripts which correspond to endogenously expressed RNA transcripts. U.S. Pat. No. 5,283,184 describes the co-suppression of the endogenous chalcone synthase gene in petunia and chrysanthemum by the introduction of an exogenous transgene comprising a chimeric gene encoding chalcone synthase; the disclosure of U.S. Pat. No. 5,283,184 is herein incorporated by reference. Co-suppression of a number of plant genes has been reported; these genes include the petunia dihydroflavonol-4-reductase gene [van der Krol et al., Plant Cell 2: 291 (1990). However, co-suppression of a plant ACC synthase gene is heretofore undescribed.

Co-suppression is a form of homology-dependent gene silencing [for review see Matzke and Matzke, Plant Physiol. 107: 679 (1995)]. Co-suppression or sense suppression may involve the coordinate repression (silencing) of a transgene and a homologous endogenous gene or the repression of two homologous transgenes. While the invention is not limited to a particular theory, it is believed that co-suppression may involve posttranscriptional events such as the induction of RNA degradation by the overexpression of a given transcript (due to expression of both the endogenous RNA and the transgene RNA transcripts). Additionally, the interaction of the transgene and the endogenous gene may occur on a DNA-DNA level which results in the methylation of the gene sequences; methylated gene sequences are often transcriptionally inactive in plants.

Regardless of the exact mechanism, the introduction of a transgene capable of expressing sense ACC synthase transcripts can be used to inhibit expression of ACC synthase in papaya. Inhibition of the ACC synthase enzyme leads to a reduction in ethylene production in the papaya fruit.

III. Isolation of Papaya Fruit-Specific ACC Synthase Genes

The present invention provides papaya fruit-specific ACC synthase gene sequences. The papaya ACC synthase cDNA was isolated by screening a cDNA library using degenerate primers corresponding to consensus sequences derived from comparison of several non-papaya ACC synthase genes. The papaya fruit-specific ACC synthase cDNA sequences can be used to isolate the corresponding genomic ACC synthase gene sequences. Genomic sequences are isolated by screening a genomic library containing papaya DNA with all or a portion of the papaya fruit-specific ACC synthase cDNA sequences (SEQ ID NO:1). In addition to permitting the isolation of the genomic papaya ACC synthase gene, the papaya fruit-specific ACC synthase cDNA sequences permit the isolation of other ACC synthase genes in papaya. As discussed above, multiple ACC synthase genes are found in plants and only a subset of these genes are involved in fruit ripening. The papaya fruit-specific ACC synthase cDNA can be used to screen cDNA libraries made using RNA from non-fruit plant tissues and in particular from non-fruit tissues (i.e., plant tissues other than fruit tissues such as stems, leaves, roots, etc.) treated to increase the expression of ACC synthase (i.e., treatment with high auxin concentrations, anaerobiosis, drought, chilling, viral infection, cadmium and lithium, physical wounding, etc.).

IV. Expression of Papaya ACC Synthase Gene Sequences

The papaya ACC synthase gene sequences of the invention allow the expression of these sequences in host cells. The coding region of the ACC synthase cDNA (i.e., the structural gene sequences; SEQ ID NO:1) is placed in operable combination with a promoter active in the host cell to permit expression of sense or antisense RNA transcripts. The promoter may be a constitutive (continuously active) or inducible promoter. Additional DNA sequences may be employed including transcription termination signals. The transcription termination region can be provided downstream from the structural gene to provide for efficient termination. The termination region may be obtained from the ACC synthase gene or from a different gene, the choice of termination region being primarily one of convenience.

The choice of promoter is governed by the type of host cell to be utilized. Promoters which are active in plant cells include: the octopine synthase promoter, the nopaline synthase promoter and the mannopine synthase promoter from the Ti plasmid and promoters from other open reading frames in the T-DNA, such as ORF7, etc.; the 35S promoter from cauliflower mosaic virus (CaMV), the double 35S promoter (D35S), the ribulose-1,3-biphosphate carboxylase small subunit promoter, phaseolin promoter, the 2AII promoter (described in WO 88/09334), the tomato hsp80 promoter (described in U.S. Pat. No 5,187,267, the disclosure of which is herein incorporated by reference). Other promoters active in plant cells are known to the art.

The promoter region will be within about 100 bp of the first base of the mRNA, more usually within about 50 bp of the first base. The termination region will usually be within about 200 bp of the last base of the structural gene, more usually within about 100 bp of the last base of the structural gene.

Depending upon the manner in which the expression cassette comprising the promoter region structural gene and termination region are to be integrated into the plant cell genome, additional DNA sequences may be involved. Where the Ti-or Ri-plasmid are employed, the expression cassette will normally be joined to at least the right border of T-DNA, and usually both borders of T-DNA. The T-DNA expression cassette construct will then be introduced into a Ti- or Ri-plasmid, conveniently by conjugation and homologous recombination. This technique has been extensively described in the literature, see, for example, Comai et al., Plasmid (1983) 10: 21–30, PCT Publication Nos. WO84/02913, 02919, 02920 and EPO Publication 0 116 418. Alternatively, binary vectors may be employed, where the Ti- or Ri-plasmid of the Agrobacterium may or may not have a T-region homologous with the T-DNA of the construct. In either event, so long as the vir genes are present on an endogenous plasmid, the T-DNA can be transferred successfully to the plant.

The expression construct will normally be joined to any other sequences of interest, such as the T-DNA sequences, in conjunction with prokaryotic or vector DNA for cloning in a bacterial host. These vectors may then be used directly for introduction into the plant genome by such techniques as (1) electroporation, (2) cocultivation, (3) microinjection, (4) particle bombardment, or the like. These techniques have been described in the literature, see, for example: (1) Fromm et al. *PNAS* (1985) 82: 5824–5828; (2) Horsch et al. *Science* (1985) 228: 1229–1231, Herrera-Estrella et al. *Nature* (1983) 303: 209–313; and (3) Crossway et al. *Biotechniques* (1986) 4: 320–334, Lin, *Science* (1966) 151: 333–337, and Steinkiss and Stabel, *Protoplasma* (1983) 116: 222–227; and (4) Charest et al., *Plant Cell Rep.* 12: 189 (1993) and Russell et al., *In Vitro Cell. Develop. Biol.* 28P:97 91992).

A large number of vectors are available for replication in bacterial hosts. A number of these vectors are commercially available, such as λkgt10 and 11, the pUC series, M13 series, pBR322, pACYC184, or the like. The selection of vector will be dependent upon preparative convenience, availability, copy number, size, and the like.

At each state, the various fragments may be manipulated by endonuclease restriction, in vitro mutagenesis, primer repair, resection, e.g. Bal31, tailing with TdT, ligation with linkers or adapters, or the like. Mutagenesis may be employed for deletions, insertions, removing or introducing a convenient restriction site, or the like. The steps are amply described in the literature, and need not be expanded upon here.

Once the construct is formed, it may be introduced into the plant cell in accordance with conventional ways as described above. Usually, the expression cassette will be joined to a marker which allows for selection of the expression cassette in the plant cell. Various markers exist which find use in plant cells, particularly markers which provide for antibiotic resistance. These markers include resistance to G418, hygromycin, bleomycin, kanamycin and gentamicin. These genes will normally be under the transcriptional initiation control of constitutive promoters, such as some of the promoters described previously. After transforming the cells, those cells having the construct will be selected by growing in a selected medium, ultimately providing for the production of callus, where cell suspensions have been used during the transformation. Shoots may then be isolated from the callus and grown in appropriate medium to produce plants. Alternatively, explants such as leaf disc or embryos may be transformed, selected by growing in a selective medium. Regenerated shoots may then be isolated and grown in appropriate medium to produce plants.

Introduction of transgenes comprising papaya ACC synthase gene sequences capable of producing antisense RNA transcripts into papaya cells permits the inhibition of the expression of the endogenous papaya ACC synthase gene through the mechanism of antisense inhibition. In this manner, the amount of ACC synthase enzyme present in the papaya fruit is reduced resulting in decreased ethylene production and delayed ripening. Ripening may be induced in these transgenic fruits by exposure of the transgenic fruit to an exogenous source of ethylene (in this manner the non-ripening phenotype of the transgenic fruit is reversed).

Introduction of transgenes comprising papaya ACC synthase gene sequences capable of producing sense RNA transcripts into papaya cells permits the inhibition of the expression of the endogenous papaya ACC synthase gene through the mechanism of co-suppression. In this manner, the amount of ACC synthase enzyme present in the papaya fruit is reduced resulting in decreased ethylene production and delayed ripening. Ripening may be induced in these transgenic fruits by exposure of the transgenic fruit to an exogenous source of ethylene.

Additionally, expression constructs containing papaya ACC synthase cDNA sequences (SEQ ID NO: 1) may be used to direct the expression of the ACC synthase enzyme in a variety of host cells, including plant and yeast cells.

V. Production Of Ethylene By Genetically Engineered Host Cells to Permit Ripening of Transgenic Fruit The inhibition of ethylene production in climacteric fruits, such as papaya and tomato, by recombinant DNA technology will create a demand for a convenient method to supply consumers of these modified fruits with a source of ethylene to permit ripening. The ACC synthase cDNA sequences of the present invention may be used in conjunction with ACC oxidase gene sequences to provide for genetically engineered host cells, such as yeast cells, which are capable of producing exogenous ethylene to permit the ripening of harvested fruit which do not produce sufficient levels of endogenous ethylene to permit ripening.

The structural gene sequences encoding the ACC synthase (e.g., SEQ ID NO:1) and ACC oxidase (e.g., SEQ ID NOS:14 and 15) enzymes are placed in expression constructs active in the host cell of choice. When the host cell chosen is a yeast host cell, the expression constructs may utilize a variety of promoters known to be active in yeast cells such as the CYC1 promoter and the PGK promoter. Termination regions may be employed downstream of the structural gene sequences to provide for efficient termination. Expression constructs containing the ACC synthase and ACC oxidase genes are introduced into the host cell using any of the standard techniques appropriate for the chosen host cell. When yeast cells are chosen as the host cell, the DNA may be introduced by electroporation or transformation with lithium acetate.

The expression constructs (i.e., one encoding ACC synthase and one encoding ACC oxidase) may be co-transformed into a host cell, the expression constructs may be subsequently introduced into the host cell or alteratively each expression plasmid may be introduced into separate host cells and the host cells may be combined (e.g., generation of a diploid yeast strain) to produce a host cell containing both expression plasmids. The resulting host cell contains the enzymes necessary for ethylene biosynthesis.

To produce ethylene on demand to permit the ripening of transgenic fruit incapable of production of sufficient levels of ethylene to permit ripening, the host cells capable of expressing ACC synthase and ACC oxidase are permitted to grow under conditions which allow for the expression of both ethylene biosynthetic enzymes and thus permit the production of ethylene.

For example, yeast cells capable of expressing both the ACC synthase and ACC oxidase genes are supplied to the consumer in a dried and inactive state. The engineered yeast cells are placed in growth medium which results in the expression of the biosynthetic enzymes and the production of ethylene. The growing yeast are placed in a sealed container with the transgenic fruit to permit ripening of the fruit.

For convenience, this system could be incorporated into the packaging used to wrap, display or ship the fruit. The production of genetically engineered host cells capable of the production of ethylene is not limited to the use of yeast host cells. Any organism capable of transformation with a vector(s) capable of expressing an ACC synthase and an ACC oxidase enzyme can be used. For example, the host cell may comprise fungi, bacteria, plants or algae. The ACC synthase and ACC oxidase gene sequences may be derived from any source (i.e., these gene sequences are not limited to the papaya gene sequences, and constructs containing the same, described herein).

EXPERIMENTAL

The following examples serve to illustrate certain preferred embodiments and aspects of the present invention and are not to be construed as limiting the scope thereof.

In the disclosure which follows, the following abbreviations apply:°C. (degrees Centigrade); g (gravitational field); vol (volume); w/v (weight to volume); v/v (volume to volume); BSA (bovine serum albumin); HPLC (high pressure liquid chromatography); DNA (deoxyribonucleic acid); cDNA (complementary DNA); RNA (ribonucleic acid); mRNA (messenger ribonucleic acid); polyA$^+$ RNA (polyadenylated RNA); LiCl (lithium chloride); p (plasmid); μl (microliters); ml (milliliters); μg (micrograms); pmoles (picomoles); mg (milligrams); M (molar); mM (milliMolar); μM (microMolar); nm (nanometers); kdal (kilodaltons); OD (optical density); EDTA (ethylene diamine tetra-acetic acid); FITC (fluorescein isothiocyanate); SDS (sodium dodecyl sulfate); 20 X SSC (3M NaCl, 0.3M Na$_3$citrate, pH 7.0); NaPO$_4$ (sodium phosphate); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA) ; PBS (phosphate buffered saline); PPBS (phosphate buffered saline containing 1 mM PMSF); PAGE (polyacrylamide gel electrophoresis); Tween (polyoxyethylene-sorbitan); Bio-Rad (BioRad Laboratories, Richmond, Calif.); BTX (Biotechnologies and Experimental Research, Inc., San Diego, Cailf.); Clonetech Laboratories (Clonetech Laboratories, Inc., Palo Alto, Calif.); Fuji Medical (Fuji Medical Systems, Stanford, Conn.); GibcoBRL (Gaithersburg, Md.); Pharmacia (Pharmacia Biotech, Piscataway, N.J.); National Biosciences (Plymouth, Minn.); New England Biolabs (New England Biolabs, Beverly, Mass.); Novagen (Novagen, Inc., Madison, Wis.); MSI Corp. (Micron Separations, Inc., Westboro, Mass.); Perkin Elmer (Norwalk, Conn.); Promega (Promega Corp., Madison, Wis.); Savant Instruments (Savant Instruments, Farmingdale, N.Y.); Stratagene (Stratagene Cloning Systems, La Jolla, Cailf.); USB (U.S. Biochemical, Cleveland, Ohio).

All chemicals and enzymes were obtained from Fisher Scientific (Pittsburgh, Pa.) unless otherwise indicated. Radioisotopes were obtained from DuPont NEN (Boston, Mass.).

EXAMPLE 1

Isolation of Papaya Fruit-Specific ACC Synthase

In order to isolate ACC synthase gene sequences involved in the ripening of papaya, a cDNA library was prepared from papaya fruit tissue and screened using degenerate oligonucleotide primers corresponding to consensus sequences derived from ACC synthase cDNA genes. This example involved a) the isolation of mRNA, b) construction of a cDNA library a) Isolation of mRNA Total RNA was isolated from 300 g of mesocarp tissue from approximately 30% yellow papaya (*Carica papaya* L.) variety 'Sunrise' using the method of Su and Gibor [Anal. Biochem. 174: 650 (1988)] as modified by Lopez-Gomez and Gomez-Lim [J. Plant Physiol. 141: 82 (1992)] as follows. Briefly, the papaya fruit tissue was cut into small pieces and quickly frozen in liquid nitrogen. The tissue was then powdered by grinding for about 2 minutes in a coffee mill (Salton Model GC-5; Salton Maxam Housewares Group, Mt. Prospect, Ill.) with a small piece of dry ice. The powdered fruit tissue (300 g) was added to 750 ml of 2% SDS, 1% P-mercaptoethanol, 50 mM EDTA, 150 mM Tris-borate (pH 7.5) and homogenized using a tissue homogenizer (Tekmar, Cincinnati, Ohio). After 5 minutes of homogenization, 0.25 volumes of 95% ethanol and ⅛th volume of 5M potassium acetate were added to the extract and homogenization was continued for 1 minute. The homogenate was extracted with an equal volume of chloroform and the aqueous phase was recovered after centrifugation at 20,000 x g for 10 minutes. The aqueous phase was extracted with an equal volume of phenol followed by extraction with phenol:chloroform (1:1) and then by extraction with chloroform with the aqueous phase being recovered as described above. The RNA was precipitated by adding LiCi to a final concentration of 3M and incubating at −20° C. over night. The RNA was recovered by centrifugation at 20,000 X g for 90 minutes at 4° C. and redissolved in water. A total of 12.24 mg of total RNA was recovered.

Messenger RNA (polyA$^+$ RNA) was isolated using the PolyATtract® mRNA isolation system IV (Promega). A total of six isolation were done as follows. For each isolation, 0.57 to 1.0 mg total RNA was dissolved in 800 μl of RNase-free water. After heating at 65° C. for 10 minutes, 3 μl of 50 pmole/ml biotinylated oligo(dT) and 20.7 μl of 20 X SSC were added and the mixture was allowed to slowly cool to room temperature over a period of approximately 30 minutes. An aliquot of streptavidin paramagnetic particles (provided in the PolyATtrack® mRNA Isolation System IV) was washed 3 times in 0.5 X SSC and resuspended in 0.1 ml of 0.5 X SSC. The RNA solution containing the biotinylated oligo(dT) was added to the washed streptavidin paramagnetic particles. After a 10 minute incubation at room temperature (i.e., 23°–26° C.), the paramagnetic particles along with the trapped mRNA were captured to the side of the tube using a magnet.

The supernatant was removed and the particles were washed four times with 0.1 X SSC (0.3 ml/wash). The mRNA was recovered by suspending the particles in 100 μl RNase-free water and removing the water while the particles were captured on the side of the tube. In a second recovery, three of the tubes were eluted sequentially with 300 μl and the other three tubes were sequentially eluted with an additional 300 μl of water. A final elution was carried out by adding 700 μl of water sequentially to each of the six tubes. All of the elution fractions were mixed and, after the addition of 1/10th volume of 3M sodium acetate, the mRNA was recovered by precipitation with an equal volume of isopropanol. Approximately 16 μg of mRNA was recovered from 5 mg of total RNA.

b) Construction of a cDNA Library

First and second strand cDNA was synthesized using the ZAP-cDNA synthesis kit (Stratagene). Six milligrams of mRNA in 20 μl of water was incubated at 65° C. for 5 minutes. Two microliters of 100 mM methyl mercury was added and incubated at room temperature for 10 minutes. Four microliters of 700 mM β-mercaptoethanol was added and the incubation was continued for an additional 5 minutes. To the denatured mRNA, 5 μl of 10 X first strand buffer (provided in the kit), 5 μl of 100 mM dithiothreitol, 3 μl nucleotide mixture (10 mM each dATP, dGTP, TTP and 5-methyl-dCTP), 2 μl of 1.4 μg/μl linker-primer 5'-GAGAGAGAGAGAGAGAGAGA ACTAGTCTCGAGTTTTTTTTTTTTTTTTTT-3' (SEQ ID NO:3), 1 μl RNase block and 5 μl of water. The reaction was incubated at room temperature for 10 minutes to anneal the primer to the mRNA and then 2.5 μl of 20 U/μl M-MuLV RT reverse transcriptase was added. Five microliters of this reaction mixture was removed to a tube containing 0.5 μl of 800 Ci/mmole [(α-$^{32}$P]dATP. Both reactions were incubated at 37° C. for 1 hour. The labeled reaction was frozen at −20° C. for later gel analysis. To the 45 μl main reaction , 40 μl of second strand buffer, 15 μl of 100 mM dithiothreitol, 6 μl of nucleotide mixture (10 mM dATP, dGTP, TTP and 26 mM dCTP), 268.3 μl water and 2 μl of 800 Ci/mmol [α-$^{32}$P] dATP. After mixing, 4.5 μl of 1 U/μl RNase H and 19.2 μl of 5.2 U/μl *E. Coli* DNA polymerase I were added and the reaction was incubated at 16° C. for 2.5 hours. The reaction was extracted with 400 μl of phenol:chloroform (1:1); the phases were separated and the aqueous phase removed and re-extracted with chloroform and the aqueous phase recovered as above.

The double-stranded cDNA was recovered by precipitation overnight (i.e., 16–20 h) at −20° C. after the addition of 33.3 μl of 3M sodium acetate and 867 μl of 100% ethanol. The precipitate was recovered by centrifugation at 13,000 x g in a microcentrifuge at 4° C. for 60 minutes. The precipitate was washed with 1 ml of 80% ethanol and recovered by centrifugation at room temperature at full speed (13,000 x g) in a microcentrifuge. The supernatant was removed, the precipitate was dried under vacuum and dissolved in 45 μl of water. Three microliters of the resuspended double-stranded cDNA was removed and frozen at −20° C. until analyzed by gel electrophoresis.

To the remaining 42 μl of the double-stranded cDNA, 5 μl of 10 X Klenow buffer (buffer #3; supplied by Stratagene), 2.5 μl of 2.5 mM nucleotides (dCTP, dGTP, dATP and TTP), and 0.5 μl of 5 U/μl Klenow fragment were added. After 30 minutes at 37° C., 50 ml of water were added and the reaction was extracted with an equal volume of phenol:chloroform (1:1) and then chloroform as described above. After the addition of 7 μl of 3M sodium acetate and 226 μl of 100% ethanol, the blunt-ended double-stranded DNA was recovered by precipitation by incubation on ice for 30 minutes and microcentrifuging at full speed at 4° C. for 60 minutes. The pellet was washed with 300 µl of 80% ethanol, centrifuged and dried as before. Seven microliters of 0.4 µg/µl EcoRI linkers were added to the dried cDNA. The EcoRI linkers comprise: 5'-AATTCGGCACGAG-3' (SEQ ID NO:4) and 5'-CTCGTGCCG-3'.

After vortexing the tube to resuspend the cDNA, 1 µl of 10 X ligation buffer, 1 µl 10 mM ATP and 1 ml of 4 Weiss U/µl T4 DNA ligase was added and the reaction was incubated over night at 8° C. The ligase was inactivated by heating at 70° C. for 30 minutes. The 5' ends of the EcoRl linkers attached to the cDNA were phosphorylated using polynucleotide kinase. One microliter of 10 X buffer #3, 2 µl of 10 mM ATP, 6 µl of water and 1 µl of 10 U/µl T4 polynucleotide kinase were added to the ligation reaction. After 30 minutes at 37° C. the kinase reaction was stopped by heating the reaction at 70° C. for 30 minutes. XhoI "sticky ends" were generated at the end of the cDNA corresponding to the 3' end of the mRNA by digestion of the XhoI site in the linker-primer (see above). Twenty-eight microliters of XhoI buffer and 3 µl of 40 U/µl XhoI were added to the cDNA and the reaction was incubated at 37° C. for 1.5 hours. The cDNA with EcoRI sticky ends at the 5' end and XhoI sticky ends at the 3' end (relative to the original mRNA) were size fractionated by passage through a Sephacryl S-400 spin column prepared as follows. Five microliters of 10 X STE [100 mM Tris (pH 7.0), 5 mM EDTA and 100 mM NaCl] was added and the cDNA was applied to the top of a 1 ml syringe containing Sephacryl S-400 (Pharmacia). A 500 µl microcentrifuge tube was placed on the bottom of the syringe and the column was placed in a centrifuge tube and centrifuged at about 400 x g for 2 minutes. Sixty microliters of 10X STE was added to the top of the syringe, a new microcentrifuge tube was placed on the bottom and the column was again centrifuged as before. This process was repeated until six fractions had been collected.

About 10% of each fraction was electrophoresed on a 1% agarose gel to determine the size distribution of the cDNA in each fraction. The remainder of each fraction was extracted with an equal volume of phenol:chloroform and then chloroform as described above and then precipitated by the addition of 2 volumes of 100% ethanol. After overnight incubation at -20° C. the cDNA was recovered by centrifugation in a microcentrifuge at full speed at 4° C. for 60 minutes. The cDNA was washed with 200 µl of 80% ethanol as described above and dried. The cDNA was dissolved in 5 µl of water and 0.5 µl was removed as used to determine the cDNA concentration using a fluorometer (Hoefer TKO 100 DNA Fluorometer). The remaining 9.5 µl of fraction 1, containing the largest cDNA molecules, contained about 304 ng of cDNA.

One-hundred nanograms of cDNA from fraction 1 was ligated into 1 µg of Uni-ZAP™, a lambda ZAP vector digested with EcoRI and XhoI (Stratagene). Fraction 1 cDNA (2.9 µl) was added to 0.54 µl of 10 x ligation buffer, 0.5 µl 10 mM ATP, 1 µl of 1 µg/µl Uni-Zap XR vector and 0.5 µl of 4 Weiss U/µl T4 DNA ligase. The reaction was incubated at 8° C. for about 44 hours. A 1 µl aliquot of the ligation reaction was added to one aliquot of the 'Freeze-Thaw' extract from the Gigapack II Gold packaging kit (Stratagene). Fifteen microliters of Sonic extract was added and the contents were gently mixed. The packaging was carried out at room temperature for 2 hours. After 2 hours, 500 µl of SM buffer and 20 µl of chloroform was added to each packaging reaction, the debris was removed by a short centrifugation in a microcentrifuge and the packaged phages were stored at 4° C. until used.

c) Identification and Construction of Oligonucleotides Homologous to Papaya ACC Synthase Genes Thirty-seven sequences encoding ACC synthase genes from 13 different plant species were retrieved from GenBank (Table 1). After preliminary analysis, 29 coding sequences from 12 species were aligned to locate regions of conservation between the reported ACC synthase genes. Five regions with high consensus were identified and were used to design degenerate oligonucleotide primers to be used in the polymerase chain reaction (PCR).

Six synthetic degenerate oligonucleotide primers were synthesized (SEQ ID NO:5-10); the sequence of these primers is shown in FIG. 2. The primer numbers represent the start position of the sequence in the consensus sequence generated from comparison of the 29 ACC synthase coding sequences. Two of the primers are complementary to the ACC synthase coding region near the 5' end of the sequence and permit extension toward the 3' end of the coding region (forward primers). The remaining four primers are complementary to sequences located throughout the body of the gene and permit extension toward the 5' end of the coding region (reverse primers). Pairs of these six primers were used in the PCR to amplify papaya ACC synthase encoding sequences from about 5 ng of first-strand cDNA made as described above.

The polymerase chain reaction was carried out in 50 µl reactions containing 50 mM KCl, 10 mM Tris-HCl (pH 9.0), 0.1% Triton X-100, 2.5 mM $MgCl_2$, 1 mM of each of the four deoxyribonucleotide triphosphates, 1 µM each of two primers and 1.5 units of Taq DNA polymerase (Promega). Thermal cycling was performed by denaturation at 95° C. for 1 min., annealing at 50° C. for 1 min. and extension at 72° C. for 2 min. Thirty-five cycles were used. Either of the two forward primers, ACS167 or ACS289, were used with one of the reverse primers, (ACS309, ACS665, ACS885 and ACS 1290) as shown in Table 2. The size of the products of each PCR reaction were measured by agarose gel electrophoresis using SeaPlaque agarose (FMC) and a commercially available 123 bp ladder as a size marker (GibcoBRL). As shown in Table 2, six of the seven possible combinations examined generated PCR products similar in size those predicted from the consensus sequence. No PCR product was observed when the primer pair comprising ACS 289 and ACS 665 were used.

d) Cloning of the Papaya Fruit-Specific ACC Synthase Gene

The 738 bp fragment obtained using primers ACS167 and ACS885 (Table 2) was purified from an agarose gel (SeaPlaque; FMC) and radioactively labeled with the Prime-a-Gene® random labeling system (Promega). The DNA fragment amplified using primers ACS167 and ACS885 corresponds to nucleotides 163 through 867 in SEQ ID NO:1 (the fragment contains extra (i.e., non-ACC synthase gene) nucleotides which terminal restriction sites).

Briefly, the 738 bp fragment was placed in a boiling water bath for 10 minutes to denature the DNA. The 50 µl random priming reaction contained about 25 ng of the denatured 738 bp fragment, 50 mM Tris-HCl (pH 8.0), 10 mM $MgCl_2$, 50 mM NaCl, 10 µl of 26 $ODU_{260}$/ml random hexadeoxynucleotides, 20 µM dATP, dGTP, TTP, 5 µl (50 µCi) [$\alpha$-$^{32}$P]dCTP (3,000 Ci/mmole) and 5 U Klenow fragment of DNA polymerase I. The reaction was carried out for 60 minutes at room temperature. The labeled DNA was separated from unincorporated dNTPs by passage through a Sephadex G50 spin column made from a 1 ml syringe as described above.

TABLE 2

Comparison of the Observed and Expected Size of PCR Products

| Primers | | Approx. size of PCR products | |
|---|---|---|---|
| Forward | Reverse | Expected | Observed |
| ACS 167 | ACS 309 | 147 | 150 |
| | ACS 665 | 488 | 492 |
| | ACS 885 | 718 | 738 |
| | ACS 1290 | 1123 | 1107 |
| ACS 289 | ACS 665 | 306 | — |
| | ACS 885 | 596 | 615 |
| | ACS 1290 | 1001 | 984 |

Approximately $6 \times 10^5$ recombinant phages were screened by plaque-lifting onto Magna nylon or NitroPure nitrocellulose membranes (MSI Corp.). Phage were plated at a density of about 280 pfu/cm² petri plate surface using *E. coli* strain XL1-Blue (Stratagene). After growth overnight, filters were placed on the petri dishes for approximately 5 minutes. The recombinant phage DNA was fixed to the membranes by placing the membranes sequentially on filter paper saturated with 0.5M NaOH and 1.5M NaCl for five minutes, then on filter paper containing 0.5M Tris-HCl (pH 8.0) and 1.5M NaCl and finally on paper containing 2 X SSC and 0.2M Tris-HCl for 30 seconds.

The DNA was cross linked to the nylon membranes using UV light (12,000 μJoules) using a UV Stratalinker 1800 (Stratagene) and baking at 80° C. for 1 hour under vacuum. The membranes were prehybridized in 50 ml of 5X SSPE, 5X Denhardt's solution, 0.5% SDS and 100 μg/ml sonicated salmon sperm DNA for 1 hour. Hybridization was carried out in 12 ml of the same buffer containing approximately 0.8 to $2 \times 10^6$ cpm of the 738-bp probe (labeled as described above) at 65° C. in a Hybaid Mark II hybridization oven. Sixteen clones were obtained which hybridized to the 738 bp ACC synthase probe.

e) Characterization of the ACC synthase cDNAs

The size of the putative ACC synthase cDNA clones was determined using the PCR; the primers used in these PCRs were homologous to the T3 and T7 promoters present in the cloning vector and that flank the cDNA insertion site: 5'-TAATACGACTCACTATAGGG-3' (T7 primer; SEQ ID NO:11) and 5'-AATTAACCCTCACTAAAGGG-3'(T3 primer; SEQ ID NO:12). Conditions for polymerase chain reaction were as described above except that each cycle comprised denaturation at 95° C. for 1 min., annealing at 55° C. for 1 min. and extension at 72° C. for 2 min. Analysis of the PCR products was conducted by agarose gel electrophoresis as described above.

The four largest clones were subjected to DNA sequencing. Initial sequencing of the 5' and 3' ends of the cDNAs was done using the Sequenase® version 2.0 DNA sequencing kit (USB) with either the T3 or T7 promoter primers. This gave about 250 bp of sequence from the 5' and the 3' ends. Two of the four longest clones were confirmed to be ACC synthase clones by comparison of the sequences present at the 5' ends of these clones with the ACC synthase genes in GenBank using a FASTA search (GCG Sequence Analysis Software Package; Genetics Computer, Inc., Madison, Wis.). For example, comparison of the papaya clone sequence with the mung bean ACC synthase revealed 70.4% identity. Analysis of these papaya ACC synthase cDNA clones revealed that about 150 bp located at the 5' end of the coding region was missing. Accordingly, the papaya fruit cDNA library was rescreened to obtain full length clones (i.e., clones containing the entire coding region).

A cDNA containing the entire coding region and 5' untranslated sequences was recovered by screening about $2 \times 10^5$ clones in the primary library with a 22-base synthetic oligonucleotide complementary to the coding strand and labeled at the 5' end using polynucleotide kinase. The sequence of this 22-mer was derived from near the 5' end of the longest clone previously sequenced. The sequence of this probe is 5'-TGAATTCAGCTGCTCCTTGTCT-3' (SEQ ID NO:13) and is positioned between bases 244 and 266 shown in FIG. 1. Hybridization screening of the library was done as described above with the exception that the hybridization temperature was 55° C. This potentially full-length cDNA was completely sequenced starting with the T3 promoter homologous primer using automated DNA sequencing at the University of Hawaii Biotechnology Service Facility. New sequencing primers were synthesized based on sequences near the end of the previous sequence until the entire strand was sequenced. This sequence was then used to make a series of primers for sequencing the opposite strand. In this manner the entire sequence of the largest ACC synthase cDNA was obtained (FIG. 1 and SEQ ID NO:1). The deduced amino acid sequence of the papaya ACC synthase protein is listed in SEQ ID NO:2.

The complete sequence of the papaya ACC synthase cDNA clone was compared with non-papaya ACC synthase genes present in GenBank; no previously reported ACC synthase gene was found to display greater than 71% identity to the papaya ACC synthase cDNA when sequences 1500 bp or larger were compared. As shown in Example 2 below, the mRNA complementary to the papaya ACC synthase cDNA (SEQ ID NO:1) is expressed in the ripening papaya fruit in a pattern consistent with its role in fruit ripening.

EXAMPLE 2

Expression of Papaya ACC Synthase in Ripening Fruit

To demonstrate that the cloned papaya ACC synthase cDNA is involved in the ripening of the fruit, the expression of mRNA complementary to the papaya ACC synthase cDNA gene of SEQ ID NO1: was examined by Northern blotting.

Messenger RNA was isolated from papaya fruits (cv 'Sunrise') at 7 different stages if ripening; immature green (green skin and white seeds with watery embryos), mature green (green skin and seeds beginning to turn brown), color break (black seeds with skin beginning to turn yellow), 20% yellow, 40% yellow, 70% yellow and 100% yellow.

The skin and endocarp were removed from the fruits and 100 g of mesocarp derived from fruits at the 7 stages listed above was frozen in liquid nitrogen and stored at −70° C. Total RNA and mRNA were isolated from the frozen tissues as described above in Example 1.

Messenger RNA from the various stages (4.2 μg each) was dried by vacuum centrifugation in a Speed Vac Sc 110 (Savant Instruments). The RNA was suspended in 15 μl of 1 X loading buffer (0.72 ml formamide, 0.16 ml 200 mM morpholinopropanesulfonic acid at pH 7.0 [10 X MOPS buffer], 0.26 ml formaldehyde, 0.18 ml water, 0.1 ml 80% glycerol and 0.08 ml of saturated bromophenol blue) containing 10 μg/ml ethidium bromide. The mixture was heated at 65° C. for 5 minutes and then placed on ice. The mRNA was dissolved in 1 X MOPS buffer and electrophoresed on a 1% formaldehyde agarose gel (Maniatis et al. 1982). Electrophoresis was done at 50 mV in 1 X MOPS buffer until the leading dye had migrated about ¾ the way to the bottom of the gel.

After electrophoresis, the gel was rinsed with two changes of water followed by two washes with 20 X SSC for 30 minutes each. 1 X SSC contains 0.15M NaCl and 0.015M sodium citrate at pH 7.0. The RNA was transferred to a Magna Nylon membrane (MSI) by vacuum transfer using a Trans-Vac™ vacuum blotter TE 80 (Hoefer Scientific Instruments). Transfer was done for 5 hours at 25 cm Hg using 20 X SSC as the buffer. The membrane was washed in 5 X SSC at 60° C. After drying under vacuum at 80° C. the RNA was fixed by treatment with 20,000 µJ of UV light using a Stratalinker™ (Stratagene).

The Northern blot was pre-hybridized at 65° C. for 2 hours in a hybridization oven (Hybaid Mark II) in 50 ml pre-hybridization buffer (6 X Denhardt's solution, 5 X SSPE, 0.5% SDS and 100 µg/ml of fragmented (i.e., sheared) herring sperm DNA). Fifty times (50 X) Denhardt's solution contains 5 g ficoll, 5 g polyvinylpyrrolidone, 5 g bovine serum albumin in 500 ml. Twenty times (20 X) SSPE contains 3.6M NaCl, 200 mM NaH$_2$PO$_4$(pH 7.4) and 20 mM EDTA.

The papaya ACC synthase cDNA was random labeled using the Prime-a-Gene kit (Promega) and [$^{32}$P]dATP. Unincorporated label was removed using a G-50 spin column. About 21.9×10$^6$ counts of radio-labeled probe was boiled for 5 minutes in 1 ml pre-hybridization buffer and added to the pre-hybridized membrane after removing all but 4 ml of pre-hybridization buffer. Hybridization was done at 65° C. overnight. The membrane was washed as follows. A first wash was conducted using 100 ml of 5 X SSPE containing 0.5% SDS at room temperature. The second wash was conducted using 50 ml of 5 X SSPE containing 0.5% SDS at 65° C. for 15 minutes. The third and forth washes comprised 50 ml of 1 X SSPE containing 0.5% SDS at 65° C. for 15 minutes. The final wash comprised 50 ml of 1 X SSPE containing 0.5% SDS at 65° C. for 15 minutes.

The blot was then exposed to flash activated X-ray film (Fuji Medical). The film was developed after 7 days of exposure at −70° C. The resulting autoradiograph is shown in FIG. 3.

In FIG. 3, lane 1 contains mRNA derived from immature green fruit; lane 2 contains mRNA derived from mature green fruit; lane 3 contains mRNA derived from color break fruit; lane 4 contains mRNA derived from 20% yellow fruit; lane 5 contains mRNA derived from 40% yellow fruit; lane 6 contains mRNA derived from 70% yellow fruit; lane 7 contains mRNA derived from 100% yellow fruit.

The results shown in FIG. 3 demonstrate that mRNA from which the cDNA was derived is expressed in ripening fruit in a pattern consistent with its role in fruit ripening. Using the cDNA as probe, ACC synthase mRNA was found to increase in mesocarp tissue starting at about the mature green stage, peaking between the 40% and 70% yellow fruit stages and decreasing dramatically by the 100% yellow fruit stage. These results demonstrate that mRNA corresponding to the ACC synthase cDNA gene (SEQ ID NO:1) is expressed in a manner that is consistent with this cDNA being a fruit-ripening-specific ACC synthase.

EXAMPLE 3

Expression of Papaya Fruit-Specific ACC Synthase in Yeast

The ability of the papaya ACC synthase cDNA (SEQ ID NO:1) to direct expression of ACC synthase in yeast was examined. The coding region of the papaya ACC synthase cDNA (SEQ ID NO:1) was inserted into the expression site of the yeast expression vector pAY27 [described in U.S. Pat. No. 4,826,785, the disclosure of which is herein incorporated by reference and in Neill et al., Gene 55: 303 (1985)]. The pAY27 vector uses the yeast CYC1 promoter and transcriptional termination and processing sequences to express foreign sequences. The pAY27 vector is shown schematically in FIG. 4.

Figure 4:
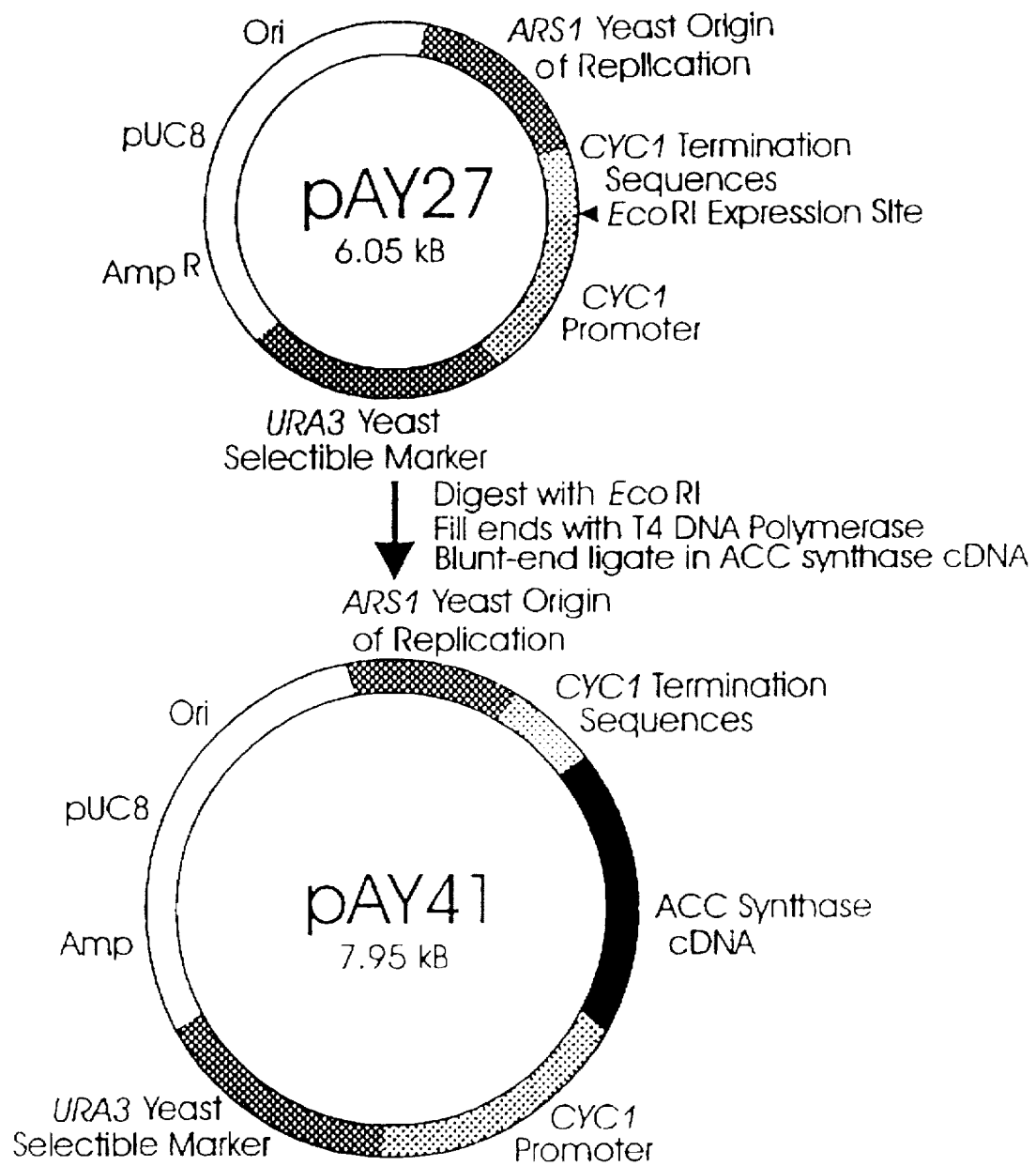
FIG. 4 depicts the construction of pAY41 from pAY27.

In FIG. 4 the following abbreviations are used: ARS [autonomous replication sequence (yeast origin of replication)]; CYC1 (the yeast iso-1-cytochrome c gene); URA3 (the yeast uracil biosynthetic enzyme, orotidine-5′-Phosphate decarboxylase); Ori (plasmid origin of replication); Amp and AmPR [ampicillin resistance gene (β-lactamase)].

FIG. 4 provides a flow diagram representing the construction of pAY41, a yeast ACC synthase expression vector, using pAY27 as the host vector. The construction was performed as follows. The ACC synthase cDNA (SEQ ID NO:1) was removed from the original cloning vector (Uni-ZAP™) by digestion with SspI and SmaI. The 1.85 kb SspI/SmaI fragment was isolated by electrophoresis on a 1% low melting agarose gel and the DNA was recovered from the gel using standard techniques [Sambrook et al., Molecular Cloning: A Laboratory Manual, 2nd ed., Cold Spring Harbor Laboratory Press, N.Y. (1989) pp.6.30–6.31]. pAY27 was digested with EcoRI, the ends were made blunt using T4 DNA polymerase and the terminal phosphates were removed by digestion with calf intestinal phosphatase using protocols and buffers supplied by the manufacturer (Promega). The prepared pAY27 vector (0.2 µg) and 0.5 µg ACC synthase cDNA were ligated in 10 µl using 1800 units of T4 DNA ligase at 16° C. for 18 hours.

The ligation products was electroporated into E. coli XL-1 Blue cells (Stratagene) using an electroporator (BTX Electroporation Unit 600). Cells were plated onto LB plates [per liter: 10 g tryptone; 5 g yeast extract; 5 g NaCl; 1 ml 1N NaOH; 1.5 g agar] containing 50 µg/ml ampicillin, 50 µl of 20 mg/ml X-gal and 10 µl of 100 mM IPTG. White colonies were recovered and plasmids isolated and restriction mapped to determine the orientation of the ACC synthase cDNA in the expression site. A plasmid containing the ACC synthase cDNA sequences in the sense orientation (relative to transcription from the yeast CYC1 promoter) was isolated and named pAY41.

pAY41 was transformed into Saccharomyces cerevisiae strain J5Y3 (α, ura3-52, trpl-289, his3-Δ1, gal2, gal10 [cir°]; obtained from Dr. John Scott, Univ. of Hawaii, Hilo, Hi.) by electroporation. Transformants were selected by plating on complete synthetic media (SD) minus uracil (described below). As a negative control, pAY27, the expression vector without the ACC synthase gene, was also transformed into S. cerevisiae strain J5Y3.

SD minus uracil medium comprises: 0.67% Bacto-yeast nitrogen base without amino acids (Difco); 2% dextrose; 20 mg/l adenine sulfate; 20 mg/l L-tryptophan; 20 mg/l L-histidine-HCl; 20 mg/l L-arginine-HCl; 20 mg/l L-methionine; 30 mg/l L-tyrosine; 30 mg/l L-leucine; 30 mg/l L-isoleucine; 30 mg/l L-lysine-HCl; 50 mg/l L-phenylalanine; 100 mg/l L-glutamic acid; 100 mg/l L-aspartic acid; 150 mg/l L-valine; 200 mg/l L-threonine and 375 mg/l L-serine.

Strain J5Y3 containing pAY27 or pAY41 were grown to stationary phase in SD minus uracil. Each was then inoculated into 250 ml of YPDG [1% Bacto-yeast extract (Difco);

2% Bacto-peptone (Difco); 3% (v/v) glycerol; 0.1% dextrose]. The cultures were grown at 30° C. on a shaking incubator to a density of $OD_{600}$ of 1.0. Seventy micrograms of methionine was then added to each culture and the cultures were incubated at 30° C. for two hours. The yeast cells (approximately 1 gm) were recovered by centrifugation at 10,000 rpm for 5 minutes in a Sorvall SS34 rotor at 4° C.

ACC was extracted and assayed following the protocol of Concepcion et al. [Anal. Biochem. 100: 140 (1979)]. Briefly, the yeast cells were suspended in 5 ml/gm fresh weight of 5% suplhosalicylic acid and approximately 0.5 gm of glass beads and homogenized in a Polytron at full-speed for 5 minutes. The homogenate was centrifuged at 10,000 rpm for 10 minutes in a Sorvall SS34 rotor at 4° C. to remove cell debris and the glass beads. The supernatant was passed over a 10 ml Dowex 50($H^+$) column (J. T. Baker Chemical Co., Phillipsburg, N.J.); the column was washed with 10 ml of water and eluted with 20 ml of 2N $NH_4OH$. The eluant was lyophilized, resuspended in 0.9 ml water containing 1 µM $HgCl_2$. One tenth of one milliliter of ice cold bleach/NaOH (5% NaOCl/saturated NaOH; 2:1) was added and the mixture was vortexed for 5 sec and incubated on ice for at least 3 min before determining the ethylene produced by oxidation of ACC using a Shimadzu GC-8A gas chromatograph equipped with a 5 foot by ⅛ inch Teflon coated alumina 60/80 column. Approximately 5 ng of ACC was extracted per gram (fresh weight) of J5Y3 yeast transformed with the expression vector containing the ACC synthase cDNA sequences (pAY41). No ACC was extracted from J5Y3 yeast containing the expression vector lacking the papaya ACC synthase gene (pAY27).

The results of this analysis demonstrated that the pAY41 vector, which contains the papaya ACC synthase cDNA, directs the expression of ACC in bakers' yeast strain J5Y3. These results demonstrate the expression of one-half of the plant ethylene biosynthetic pathway in an genetically engineered yeast. As described below, co-expression of an ACC oxidase gene in yeast harboring pAY41 will result in the production of yeast cells that can synthesize ethylene.

EXAMPLE 4

Ethylene Production in Yeast Expressing the Papaya ACC Synthase and an ACC Oxidase The inhibition of ethylene production in climacteric fruits, such as papaya, by recombinant DNA technology creates a demand for a convenient method to supply consumers of these modified fruits with a source of ethylene to permit ripening. The experiment described below provides genetically engineered yeast which are capable of producing ethylene to permit the ripening of fruit which do not produce sufficient levels of endogenous ethylene to permit ripening.

In Example 3, it was demonstrated that yeast harboring the pAY41 plasmid express the ACC synthase enzyme; the ACC synthase enzyme comprises one half of the plant ethylene biosynthetic pathway. To permit ethylene production in yeast, the yeast is transformed with pAY41 and an expression vector, such as pYE13, which expresses a tomato ACC oxidase enzyme.

pYE13 contains the coding region of the tomato ACC oxidase cDNA gene (SEQ ID NO:14) inserted into the yeast expression vector pBEJ15 downstream of the phosphoglycerate kinase (PGK) promoter [Hamilton et al., Proc. Natl. Acad. Sci. USA 88: 7434 (1991)]. The ACC oxidase coding region located within SEQ ID NO:15 may also be used to provide ACC oxidase gene sequences [Spanu et al., EMBO J. 10: 2007 (1991)]. pYE13 has been shown to direct the expression of the tomato ACC oxidase enzyme in transformed yeast cells (JRY188 cells).

Alternatively an ACC oxidase cDNA can be isolated from papaya or other fruits as follows. Degenerate oligonucleotides complementary to highly conserved regions deduced from comparison of published ACC oxidase sequences were synthesized; these primers comprise: 5'-GC(C/T)CA(C/T)ACIGA(C/T)GCIGGIGG-3' (SEQ ID NO:16) and 5'-TCATIGC(T/G)(T/G)C(A/G)A(T/G)IGGTTC-3' (SEQ ID NO:17); "I" represents inosine. The primers were used to prime a PCR using cDNA synthesized from mRNA isolated from 30% ripe papaya fruits (first strand cDNA was synthesized as described in Example 1. The PCR contained 5 ng single-stranded cDNA, Taq DNA polymerase reaction buffer, 2.5 mM $MgCl_2$, 1 mM all four dNTPs and 1 µM of each primer. Thermal cycling was conducted for a total of 35 cycles comprising 94° C. for 1 min; 45° C. for 1 min and 72° C. for 2 min; a 10 min incubation was conducted at 72° C. after the last cycle. A 350 bp PCR fragment was amplified which was found to be 66% to 77% identical to published ACC oxidase gene sequences.

The 350 bp PCR product is used to screen a fruit cDNA, such as the papaya fruit cDNA library described in Example 1, to obtain a complete fruit ACC oxidase cDNA. The complete cDNA is inserted into a yeast expression vector to permit the expression of ACC oxidase in transformed yeast cells. Yeast cells are transformed using standard techniques such as electroporation or the lithium acetate method [Short Protocols in Molecular Biology, 2nd ed., Ausubel et al., eds., John Wiley & Sons. N.Y. (1992) pp. 13-29-13-32]. The transformed yeast cells are selected by growth on the appropriate selective medium; if the vector chosen is the pBEJ15 vector (as was the case for the construction of pYE13) SD medium minus leucine is used as the selective medium (SD minus leucine is made according to the recipe for SD minus uracil with the exception that the medium lacks leucine and contains 20 mg/l uracil).

Yeast cells capable of expressing an ACC oxidase gene (e.g., JRY188 cells containing pYE13) are genetically crossed with JSY3 cells containing pAY41 to yield a diploid yeast containing the entire ethylene biosynthetic pathway. Alternatively, an ACC oxidase expression plasmid, such as pYE13, is transformed into a yeast strain containing pAY41 to give a doubly transformed strain expressing both ACC synthase and ACC oxidase genes to permit the production of ethylene in yeast.

To measure ethylene production, the yeast strain containing both expression plasmids is grown in YPDG media. The air in the head space of the culture vessel is sampled by insertion of a 22 gauge needle attached to a 1 ml syringe and withdrawing 1 ml of air present over the yeast culture. Because ethylene is heavier than air, it will accumulate in the head space. The 1 ml sample collected from the head space is injected into a Shimadzu GC-8A gas chromatograph equipped with a 5 foot by ⅛ inch Teflon-coated alumina 60/80 column as described in Example 3. Ethylene is identified by its retention time on the column in relation to that of a standard ethylene gas mixture. Cultures of yeast strains containing lacking any expression plasmids or containing only one of the two ethylene biosynthetic gene plasmids are used to provide negative controls.

This example provides a genetically engineered biological system that produces ethylene upon demand; the modified yeast strain can be provided in a mixture comprising powder growth medium (e.g., YPD medium) to the consumer in a dried (i.e., inactive) form. The addition of the dried yeast/medium mixture to water allows the consumer to produce ethylene upon demand (i.e., "activates" the yeast and permits growth and ethylene production). These yeast can be used to induce the ripening of any fruit that has been manipulated by recombinant DNA or classical genetic techniques to produce no or low levels of ethylene.

EXAMPLE 5

Construction of Vectors for the Expression of Anti-Sense ACC Synthase Transcripts ACC synthase is the rate limiting enzyme in the ethylene biosynthetic pathway in climacteric fruit. In order to express anti-sense transcripts of the papaya ACC synthase gene in papaya fruit to delay ripening by reducing the amount of ACC synthase, the following expression vector was constructed.

The papaya fruit-specific ACC synthase cDNA (SEQ ID NO:1) was inserted into the pBI121-L vector. pBI121-L was created by modification of pBI 121 (Clontech Laboratories) as follows.

Two 38-base pair synthetic sequences containing lox recognition sites for the cre site-specific recombinase were inserted surrounding the neomycin phosphotransferase II (NPT II) gene of pBI121 that serves as the selectable marker; this allows for the removal of the NPTII selectable marker gene from the construct after it is integrated into the plant genome [Dale and Ow. Proc. Natl. Acad. Sci. USA 88: 10558 (1991)].

Three synthetic oligonucleotides were synthesized based on the loxP sequences defined by Dale and Ow (supra). These oligonucleotides comprised : loxA: 5'-AGC TATAACTTCGTATAGCATACATTATACGAAGTTAT-3' (SEQ ID NO:18); loxB: 5'AGCTATAACTTCGTATAAT GTATGCTATACGAAGTTAT-3' (SEQ ID NO:19) and loxC: 5'-ATAACTTCGTATAGCATACATTATACGAAG TTATAGCT-3' (SEQ ID NO:20). loxB is the complementary strand to both loxA and loxC. When loxA and loxB were annealed they formed a double-stranded molecule with 4-base overhangs complementary to HindIII overhangs which allows insertion of the double-stranded sequence into a HindIII site such as that found after the NOS transcription termination sequence in pBI121. Annealing of loxC with loxB yielded a blunt-ended double-stranded DNA containing a lox recognition site.

Synthetic lox sites were inserted surrounding the NPT II gene of pBI121 as follows. pBI121 was digested with PmeI (New England Biolabs, Beverly, Mass.) at 37° C. for 2 hours in reaction buffer supplied by the manufacturer. This cut pBI121 at the single PmeI site just in front of the NOS promoter that drives expression of the NPT II gene. The double-stranded synthetic lox site resulting from mixing equimolar amounts of loxB and loxC, heating to 95° C. in water and slowly cooling to room temperature, were ligated into the PmeI-digested pBI121. The 30 µl ligation reaction contained 1 X ligation buffer (New England Biolabs, Beverly, Mass.) 60 nmoles Pme I-digested pBI121, 3 µl of a 1 µM stock solution of annealed lox B/ lox C, 4 units Pme I and 4,000 units of high concentration T4 DNA ligase (New England Biolabs, Beverly, Mass.) at 16° C. overnight. One to 4 µl of the ligation reaction were electroporated into E. coli XL1-Blue (Stratagene) and plated onto LB plates containing 50 µg/ml kanamycin, 50 µl of 20 mg/ml X-gal and 10 µl of 100 mM IPTG. White colonies were picked to fresh LB-kanamycin master plates.

Colonies containing the lox site were identified by colony hybridization. The master plates were grown for 4 hours at 37° C., and then blotted to nylon membranes (MSI) that were then placed on fresh LB-kanamycin plates and grown at 37° C. overnight. The filters were floated on 0.5N NaOH for 10 minutes, neutralized by floating on 0.5M Tris-HCl (pH 8.0) containing 0.5M NaCi for 2 minutes and rinsed in 2 X SSC.

The filters were pre-hybridized in 20 ml of 6 X SSPE, 5 X Denhardt's solution, 0.5% SDS and 100 µg/ml fragmented herring sperm DNA at 55° C. for 3 hours. The pre-hybridization solution was replaced with 10 ml of fresh solution containing $8.4 \times 10^6$ cpm of loxC labeled at the 5' end with [$^{32}$P] using T4 polynucleotide kinase. The 50 µl labeling reaction contained 50 pmoles of loxC, 1 X polynucleotide kinase reaction buffer (Promega), 15 µl of 3,000 ci/mmol [$\gamma$-$^{32}$P] ATP and 20 units T4 polynucleotide kinase (Promega). The reaction was incubated at 37° C. for 10 minutes and the product was separated from the unincorporated ATP using a Sephadex G-25 spin column. Hybridization was at 55° C. overnight. The filters were washed at 55° C. twice in 100 ml of 2 X SSC containing 0.5% SDS, once with 100 ml of 1 X SSC containing 0.5% SDS and autoradiographed as described in Example 1.

Several colonies were found to hybridize intensely and were selected for further characterization. Plasmid DNA was extracted using the Magic Minipreps DNA Purification System® (Promega) and digested with PmeI as described above. Plasmids containing the lox site will no longer have a PmeI site. Plasmids that were resistant to digestion by PmeI were further analyzed by DNA sequencing at the University of Hawaii Biotechnology Service Center.

A plasmid containing the lox site in the desired orientation was confirmed.

This plasmid was digested with HindIII and then mixed with HindIII sticky-ended loxA/loxB, annealed as described above and ligated. The ligation reaction contained 2.5 µg of HindIII-digested plasmid, 1.25 pmoles of loxAlloxB, 1 X ligation buffer (Promega), 6 units of T4 DNA ligase (Promega), 1.25 units of HindIII in a final volume of 30 µl. The reaction was incubated at room temperature for 1 hour, heated at 80° C. for 10 min and transformed into E. coli XL1-Blue (Stratagene). Random plasmids were screened for loss of the HindII site by digestion with HindIII as above. Final confirmation was obtained by DNA sequencing as described above.

This plasmid, pBI121-L, was digested with SacI. The 173 µl reaction contained 10 µg pBI121-L, 1 X multicore buffer (Promega), and 20 units of SacI (Promega). After I hour at 37° C., 0.7 µl 25 mM dNTPs and 10 units of T4 DNA polymerase (Promega) were added. The reaction was then incubated at 15° C. for 30 minutes to blunt-end the SacI ends. After inactivation of the T4 DNA polymerase by incubation at 75° C. for 15 minutes, 24 units of SmaI were added and the reaction was incubated at room temperature for two hours. The reaction was stopped by heating at 80° C. for 15 minutes. The DNA was precipitated by the addition of 17 µl of 3M sodium acetate and 375 µl of 100% ethanol. After 1 hour at −70° C. the DNA was recovered by centrifugation in a microcentrifuge at full-speed for 20 min at 4° C. The DNA was washed with 70% ethanol and dried under vacuum. The DNA was dissolved in 88 µl water. Ten µl 10 X calf intestinal alkaline phosphatase buffer (Promega) and 20 units of calf intestinal alkaline phosphatase was added and the reaction was incubated at 37° C. for 2 hours. The reaction was stopped by the addition of 4 µl 0.5M EDTA followed by heating at 75° C. for 10 minutes. The sample was extracted once with an equal volume of phenol saturated with water, then with phenol: chloroform (1:1) and finally with chloroform. The DNA was recovered by precipitation after adding 0.1 volume of 3M sodium acetate and 2.5 volumes of 100% ethanol.

The papaya ACC synthase cDNA, described in Example 1, was released from the original plasmid by digestion with SmaI and SspI. Eight µg of cDNA plasmid was digested in a 50 µl containing 5 µl 10 X multicore buffer (Promega), 16 units SmaI and 25 units SspI. Digestion was carried out at 25° C. for I hour and then at 37° C. for 1 hour. The digestion products were separated by electrophoresis on a 1% Sea-Plaque agarose gel. The 1.8 kb papaya ACC synthase cDNA was recovered and purified using the Genclean II kit (Bioll0, Vista, Calif.). The cDNA was inserted into pBI121-L by blunt-end ligation as follows. A reaction volume of 40 µl contained 1 X ligation buffer (Promega), 1.6 µg pBI121-L, 350 ng cDNA and 12 units of T4 DNA ligase (Promega). The reaction was incubated at 16° C. overnight. Five µl of this reaction were electroporated into *E. Coli* XLI-Blue cells (Stratagene) and transformants were obtained as described above.

DNA from 24 colonies was isolated and digested with either EcoRi or BamHII and SacI to determine the presence and orientation of the papaya ACC synthase cDNA sequences in pBI121-L. One plasmid with the cDNA in the sense and one with the plasmid in the antisense direction were further analyzed by DNA sequencing of the junctions between the plasmid and cDNA to confirm the orientation. DNA sequencing was carried out as previously described. The antisense-containing plasmid, designated pACCS1, is shown in FIG. 5.

Figure 5:
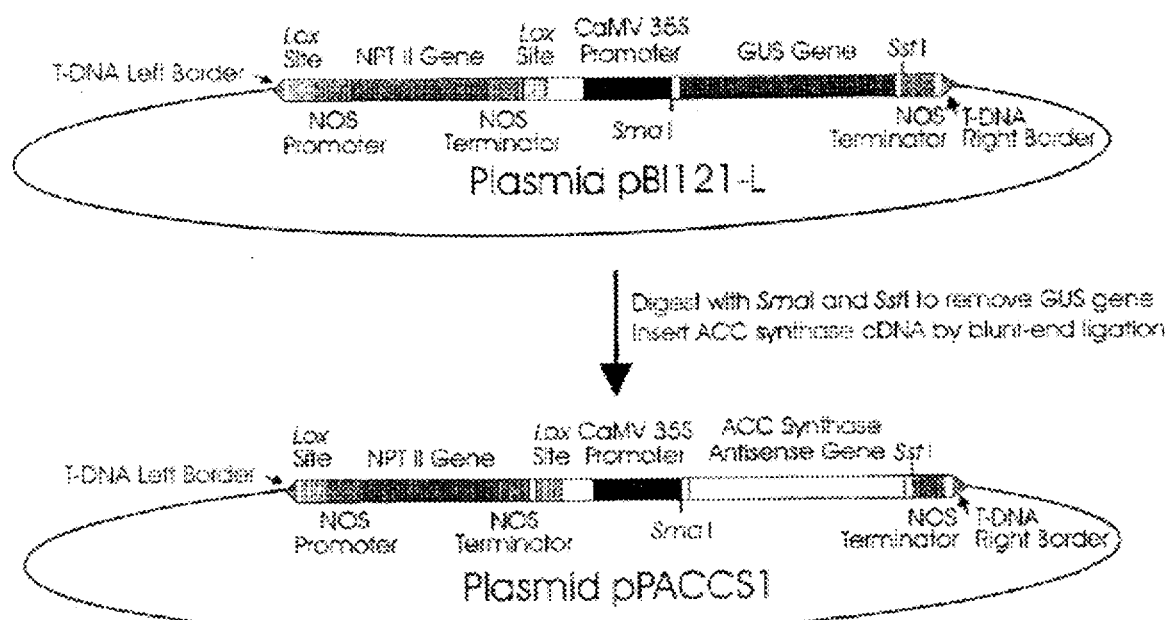
FIG. 5 depicts the construction of pPACCSI from pBI121-L.

FIG. 5 provides a schematic showing the construction of pACCS1 by the insertion of the ACC synthase coding region (in the antisense orientation) into the pBI121-L vector. In FIG. 5 the following abbreviations are used: NOS (nopaline synthase); CaMV (Cauliflower mosaic virus); GUS (β-glucuronidase) and neomyocin phosphotransferase II (NPT II).

In addition to isolation of the pACCSI construct, a sense construct, pACCS2, has also been recovered; the pACCS2 construct contains the ACC synthase cDNA sequences in the opposite orientation relative to the orientation in pACCS1. pACCS1 directs the expression of antisense transcripts and pACCS2 directs the expression of sense transcripts.

EXAMPLE 6

Expression of Anti-Sense ACC Synthase Transcripts in Papaya

The transformation vector, pACCS1 (Example 5), which expresses the anti-sense strand of the papaya fruit-specific ACC synthase cDNA, was used to transform papaya plant cells. Somatic embryos were obtained from zygotic embryos as described by Fitch el al. [Plant Cell Rep. 9: 189 (1990)]. Briefly, immature zygotic embryos were isolated from 'Sunset', 'Sunrise' and 'Kapoho' cultivars of papaya at 90 to 105 days post-pollination. One cotyledon was removed from each embryo. The embryos were incubated on induction medium consisting of one-half-strength MS media (GibcoBRL, Grand Island, N.Y.), 2.7 mM glutamine, 0.3 mM myo-inositol, full-strength MS vitamins (GibcoBRL, Grand Island, N.Y.), 6% sucrose, 45.2 µM 2,4-dichlorophenoxyacetic acid (2,4-D) and 1% agar at pH 5.8. Particle bombardment is initiated when somatic embryogenesis is observed, generally 1 to 3 months after initiation of the cultures. One week prior to bombardment 40 to 100 embryos were transferred to a 6 cm petri dish and oriented such that their apical meristems were exposed and the radicles embedded in the medium solidified with 1.5% agar.

pACCS1 was introduced into the somatic embryos as follows. Before bombardment the embryos were clustered in a 2.5 cm circle in the center of the petri dishes. For particle bombardment, 60 mg of 1.6µ gold particles (BioRad) were washed with ethanol and then water as recommended by the particle delivery system manufacturer (Bio-Rad). After washing, the particles were suspended in 1 ml water and allocated into twenty 0.5 ml microcentrifuge tubes such that each tube contained about 3 mg of gold particles. Ten to 20 µg of pACCS1 plasmid DNA was added to each tube and precipitated onto the gold particles by the addition of 50 µl of 2.5 M $CaCl_2$, 20 µl of 0.1 M spermidine and 250 µl 100% ethanol. After washing with ethanol, the particles were suspended in 60 µl of 100% ethanol and 10 µl was applied to each macrocarrier (BioRad) prior to bombardment. Each petri dish was bombarded 3 times in the Biolistic PDS-1000/He Particle Delivery System (Bio-Rad) using 1550 psi rupture discs, with a vacuum of 27 in. Hg.

After bombardment, the embryos were transferred to fresh induction medium and cultured at 25° C. in the dark. After 3 weeks of growth, the embryos were transferred to induction medium containing 75 mg/l kanamycin. After an additional 4 weeks, the embryos are transferred to induction medium containing 150 µg/l kanamycin. After about 4 months rapidly growing kanamycin-resistant somatic embryos are transferred to maturation media without kanamycin. Maturation media is identical to induction media except that it does not contain 2,4-D. Maturation media results in the germination of somatic embryos to form shoots.

After shoot formation, the shoots are excised and rooted by insertion of the cut end into solid MS media containing 4.9 µM indole-3-butyric acid. After root formation occurs, the plantlets are transferred to jars containing a 50/50 mixture vermiculite (Star Garden Store, Honolulu, HI) and liquid MS medium. Well-rooted, vigorously growing plants are transferred to potting soil for further growth.

When the papaya plants are approximately 0.5 meter tall, they are transplanted to an experimental containment field for growth to maturity. Approximately four months after transplantation to the field, flowering will commence. Flowers are tagged to record anthesis on transformed (i.e., containing pPACCSI) and on control plants of the same cultivar and on control plants containing the transformation vector lacking the anti-sense ACC synthase sequences (i.e., pBI121-L). Approximately five months after anthesis, control fruits will begin to ripen. The fruits (on transgenic and control plants) are observed for signs of ripening. Visual signs of ripening include changes in skin color (green skin turns to yellow skin in ripening fruits) and seed color (the white seeds become darker and finally turn black in ripe papaya fruit). Ripening also involves softening of the fruit which is measured using a force gauge. (accuForce Cadet, Ametek, Largo, Fla.). ACC synthases mRNA expression and accumulation is measured by Northern blotting as described in Example 2.

Ethylene production is measured in control and transgenic (i.e., anti-sense) papaya fruit at various times after anthesis. Ethylene production is measured by enclosing individual fruits in sealed jars and detecting ethylene in the head space of the jar by gas chromatography as described in Example 4. Fruit from transformed papaya plants containing the pACCSI construct will produce no or only 5% of the normal level of ethylene and will ripen more slowly as compared to control papaya fruit (i.e., unmodified papaya or papaya transformed with pBI121-L). The seeds from these papaya will be used to establish lines of transgenic papaya. Fruit produced by these transgenic lines will have the characteristics of delayed ripening (due to inhibition of endogenous ethylene production) and ripening will be inducible by exposure of the transgenic fruit to exogenous ethylene.

From the above it is clear that the present invention provides the entire papaya fruit-specific cDNA. The papaya ACC synthase cDNA allows the expression of ACC synthase in yeast. Expression of anti-sense transcripts from the papaya ACC synthase cDNA in papaya fruit tissue will allow for the inhibition of ACC synthase mRNA and therefore ripening in the modified papaya fruit.

---

What is claimed is:

1. A purified oligonucleotide comprising the nucleotide sequence set forth in SEQ ID NO:1.

2. The oligonucleotide of claim 1, wherein said nucleotide sequence further comprises 5' and 3' flanking regions.

3. The oligonucleotide of claim 1, wherein said nucleotide sequence further comprises intervening regions.

4. A recombinant DNA vector comprising the oligonucleotide of claim 1.

5. A plant cell transformed with the nucleotide sequence of claim 1.

6. A plant transformed with the nucleotide sequence of claim 1.

7. An isolated nucleotide sequence encoding the amino acid sequence set forth in SEQ ID NO:2.

8. The nucleotide sequence of claim 7, wherein said nucleotide sequence further comprises 5' and 3' flanking regions.

9. The nucleotide sequence of claim 7, wherein said nucleotide sequence further comprises intervening regions.

10. A vector comprising the nucleotide sequence of claim 7.

11. The nucleotide sequence of claim 7, wherein said nucleotide sequence is selected from the group consisting of deoxyribonucleic acid and ribonucleic acid.

12. A plant cell transformed with the nucleotide sequence of claim 7.

13. A plant transformed with the nucleotide sequence of claim 7.

* * * * *

UNITED STATES PATENT AND TRADEMARK OFFICE
CERTIFICATE OF CORRECTION

PATENT NO. : 5,767,376
DATED : 06/16/98
INVENTOR(S) : John I. Stiles *et al.*

It is certified that error appears in the above-indentified patent and that said Letters Patent is hereby corrected as shown below:

Column 32, line 7, please delete "NaCi" and insert --NaCl--.

Column 32, lines 34-35, please delete the hard return after "was confirmed.", and delete the paragraph indentation preceding "This plasmid was", such that one paragraph is formed.

Signed and Sealed this

Sixteenth Day of March, 1999

*Attest:*

*Attesting Officer*

Q. TODD DICKINSON

*Acting Commissioner of Patents and Trademarks*